US006323240B1

(12) United States Patent
Giordani et al.

(10) Patent No.: US 6,323,240 B1
(45) Date of Patent: *Nov. 27, 2001

(54) 4-PHENYL-4-OXO-BUTANOIC ACID DERIVATIVES WITH KYNURENINE-3-HYDROXYLASE INHIBITING ACTIVITY

(75) Inventors: Antonio Giordani; Paolo Pevarello, both of Pavia; Carmela Speciale, Nerviano; Mario Varasi, Milan, all of (IT)

(73) Assignee: Pharmacia & Upjohn S.p.A., Milan (IT)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/068,016
(22) PCT Filed: Oct. 16, 1996
(86) PCT No.: PCT/EP96/04518
   § 371 Date: May 1, 1998
   § 102(e) Date: May 1, 1998
(87) PCT Pub. No.: WO97/17317
   PCT Pub. Date: May 15, 1997

(30) Foreign Application Priority Data

Nov. 3, 1995 (GB) .................................................. 9522615

(51) Int. Cl.⁷ ........................ A61K 31/195; A61K 31/24; A61K 31/12; B41L 5/04; C07C 229/00
(52) U.S. Cl. .......................... 514/564; 514/563; 514/535; 514/538; 514/676; 514/678; 462/441; 560/39
(58) Field of Search ..................... 514/319, 564, 514/563, 535, 538, 676, 678; 462/444; 560/39

(56) References Cited

U.S. PATENT DOCUMENTS

| 5,519,055 | 5/1996 | Schwarcz et al. ................... 514/564 |
| 5,708,030 | 1/1998 | Schwarcz et al. ................... 514/541 |

*Primary Examiner*—Theodore J. Criares
(74) *Attorney, Agent, or Firm*—Oblon, Spivak, McClelland, Maier & Neustadt, P.C.

(57) ABSTRACT

4-phenyl-4-oxo-butanoic acid derivatives for use in the treatment of the human or animal body by therepy; particularly as kynurenine-3-hydroxylase inhibitors, in the prevention and/or treatment of a neurodegenerative disease wherein the inhibition of such an enyzme is needed. The present invention further comprises a selected class of the above mentioned 4-phenyl-4-oxo-butanoic acid derivatives, their pharmaceutically acceptable salts, a process for their preparation and pharmaceutical compositions containing them.

14 Claims, 1 Drawing Sheet

Figure 1:
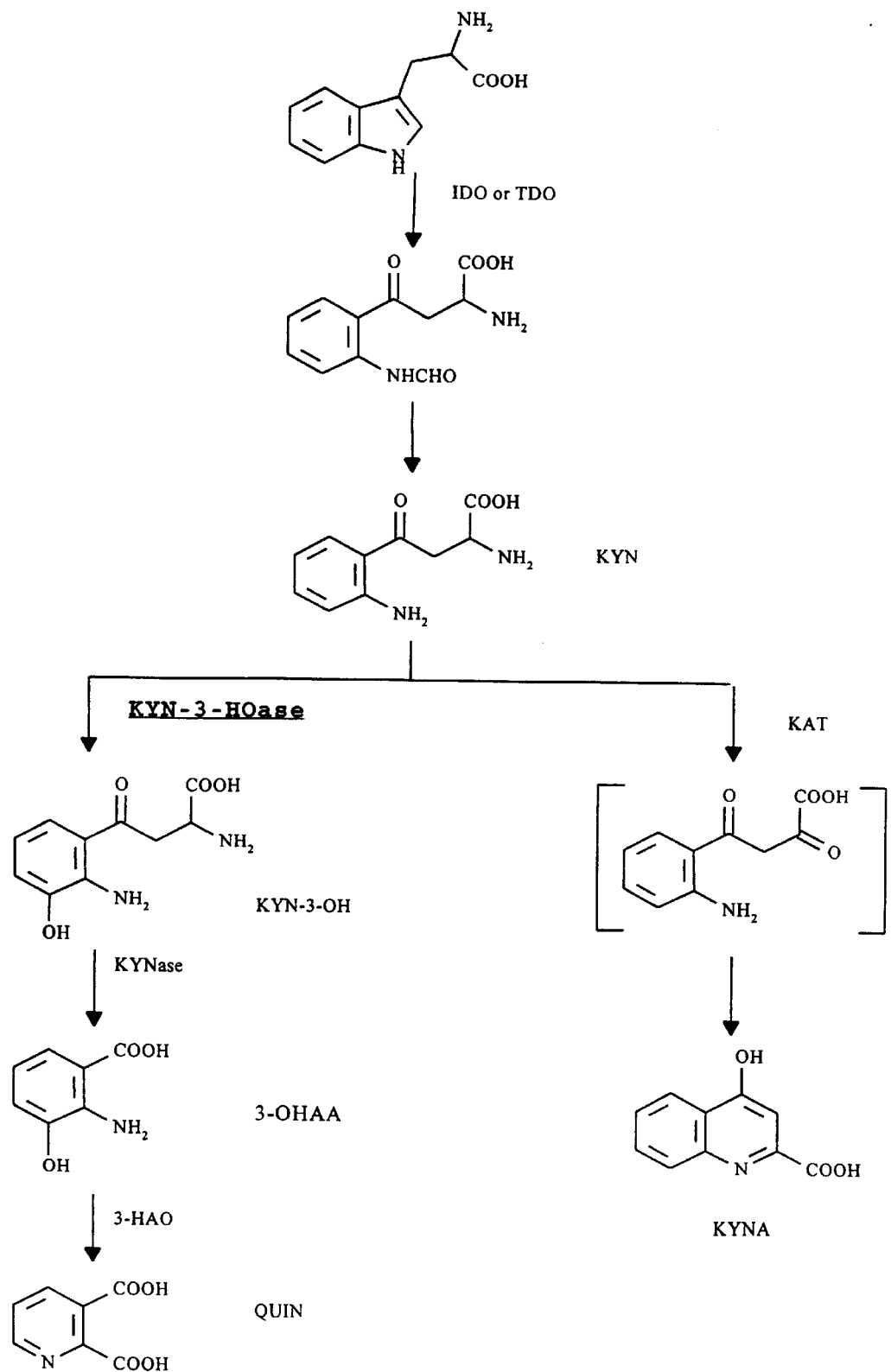

4-PHENYL-4-OXO-BUTANOIC ACID DERIVATIVES WITH KYNURENINE-3-HYDROXYLASE INHIBITING ACTIVITY

This application is a Rule 371 of PCT/EP96/04518 filed Oct. 16, 1996.

The present invention refers to the use in the prevention and/or treatment of neurodegenerative diseases, such as, for example, Huntington's chorea, Alzheimer's disease, dementia caused by acquired immunodeficiency syndrome (AIDS), infarctual dementia, cerebral ischemia, cerebral hypoxia, Parkinson's disease, epilepsy, head and spinal cord injury, amyotrophic lateral sclerosis, glaucoma/retinopathy, infections and inflammations of the brain, of 4-phenyl-4-oxo-butanoic acid derivatives which act as inhibitors of kynurerine-3-hydroxylase (KYN-3-OHase), an enzyme involved in the metabolic pathway of kynurenine.

This invention further comprises novel compounds which represent a selected class of the above mentioned 4-phenyl-4-oxo-butanoic acid derivatives, their pharmaceutically acceptable salts, a process for their preparation and pharmaceutical compositions containing them. 4-Phenyl-4-oxo-butanoic acid compounds are known in the art. For instance, British patent no. 1498903 discloses aromatic ketoacids acids useful in the prevention and treatment of inflammatory syndromes and atherosclerosis.

British patent no. 1565616 refers to 4-phenylbutyric acid derivatives having analgesic and anti-inflammatory properties. Published French patent application no. 2503140 claims diphenyl-4-oxo-4-methylene-3-butyric acid derivatives having valuable hypolipaemic properties and therefore useful as antiatherosclerotic agents. British patent no. 1068751 discloses phenolic diphenylbenzocycloalkenes having anti-inflammatory activity. U.S. Pat. No. 3,876,800 relatives to 4-(disubstituted phenyl)butyric acids and functional derivatives thereof having analgesic and anti-inflammatory properties.

FIG. 1 shows the Kynurenine pathway.

It is well known in the art that through the kynurenine (KYN) pathway, tryptophan metabolism gives rise to the formation of quinolinic acid (QUIN) on the one side and kynurenic acid (KYNA) on the other, as shown in FIG. 1.

In the last decade, several lines of evidence have demonstrated that two intermediates of the kynurenine metabolism, QUIN and KYNA, when injected in the CNS, act as a neurotoxin and as a neuroprotective agent, respectively. Consequently, the demonstration that these two metabolites of the kynurenine pathway (unable to cross the blood brain barrier), are normal constituents of the mammalian brain, reveals the existence of this pathway within the CNS and proposes the involvement of QUIN and KYNA in brain physiology and pathology (Stone T. W., Pharmacol. Rew., (1993), 310–379).

Both QUIN and KYNA are able to interact with the ionotropic excitatory amino acid receptors. In particular, QUIN is a highly selective agonist at the N-methyl-D-aspartate (NMDA) receptor (Stone T. W., Eur. J. Pharmacol., 72, (1981) 411–412), whereas KYNA is a broad spectrum antagonist of the ionotropic excitatory aminoacid receptors, preferentially acting at the glycine co-agonist site of the NMDA receptor (J. Neurochem., 52, (1989) 1319–1328).

In vitro studies have demonstrated that the exposure of neuronal cell cultures to relatively low QUIN concentrations are neurotoxic either when applied over a prolonged period of time or in combination with glutamate (Schurr A., Brain Res., 568, (1991) 199–204). In vivo QUIN has been shown to produce convulsions and axon sparing lesions that mimic the nerve cell loss described in human neurodegenerative disorders (Schwarcz R., Science, 219, (1983) 316–318). Moreover an increase in QUIN production has been demonstrated in post-ischemic gerbil brain (Saito K., J. Neurochem., 60, (1993) 180–192), following spinal cord trauma in rats (Stokes B. T., Brain Res., 633, (1994) 348–352) and in guinea pig (Blight A. R., Brain Res., 632, (1993) 314–316), and, finally, in a model of experimental allergic encephalomyelitis (Flagan E. M., J.Neurochem., 64, (1995) 1192–1196).

On the other hand, KYNA has shown anticonvulsant and neuroprotective properties in several animal models (Stone T. W. Pharmacol.Rev.45, (1993) 309–379), and, additionally, the experimentally-evoked rise of KYNA concentrations is capable to elicit neuroprotection and seizures reduction (Nozaki K., J. Cereb. Blood Flow Metab., (1992), 12, 400–407; Russi P., J. Neurochem., 59, (1992) 2076).

Notably, KYNA when co-injected with QUIN is able to prevent the excitotoxic neuronal damage evoked by the neurotoxin (Foster A. C., Neurosci. Lett., 48, (1984) 273–278). These data taken together show that KYNA may act as the brain's own defence against detrimental events, such as excitotoxicity and seizures, leading to pathological situations (Schwarcz R., Neurotoxin and neurodegenerative disease, Ann. N.Y.Sci., 140, vol. 648, 1992).

It follows that, pharmacological interventions aimed at increasing KYNA formation and/or blocking QUIN synthesis, can be useful for the therapy of excitotoxic brain diseases. Since in the kynurenine pathway (FIG. 1) KYN-3-OHase is the first enzyme involved in the formation of QUIN from KYN, compounds which act as inhibitors of this enzyme are expected to block the metabolism toward QUIN and, at the same time, to increase KYNA formation.

Consequently, compounds able of inhibiting this enzyme are useful in the prevention and/or treatment of a variety of pathologies involving quinolinic acid or excessive activation of the neurotransmission mediated by excitatory amino acid receptors.

Accordingly, the present invention provides a 4-phenyl-4-oxo-butanoic acid derivative of formula (I) either as a single isomer or as mixture of isomers

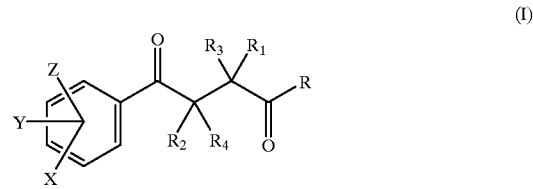

(I)

wherein

X, Y and Z are, each independently, hydrogen, halogen, cyano, nitro, $C_1$–$C_6$ alkyl, phenyl, benzyl, $C_2$–$C_4$ alkenyl, $C_2$–$C_4$ alkynyl, $C_1$–$C_6$ alkoxy or $C_1$–$C_6$ alkylthio;

R is hydroxy; —$OR_5$ in which $R_5$ is $C_1$–$C_6$ alkyl, phenyl, benzyl, $C_2$–$C_4$ alkenyl or $C_2$–$C_4$ alkynyl; —$N(R_6)_2$ or —$N(R_6)OR_6$ in which each $R_6$ is, independently, hydrogen, $C_1$–$C_6$ alkyl, $C_2$–$C_4$ alkenyl, $C_2$–$C_4$ alkynyl, phenyl or benzyl;

$R_1$, $R_2$, $R_3$ and $R_4$ are, each independently, hydrogen, halogen, hydroxy, thiol, $C_1$–$C_6$ alkoxy, $C_1$–$C_6$ alkylthio, $C_1$–$C_6$ alkyl, $C_2$–$C_4$ alkenyl, phenyl or benzyl, or $R_1$ and $R_3$ or $R_2$ and $R_4$ together form a group =$CHR_8$ in which $R_8$ is hydrogen, a straight $C_1$–$C_5$ alkyl chain or phenyl;

or a pharmaceutically aceptable salts thereof, for use in a method of treatment of the human or animal body by therapy.

Typically, the 4-phenyl-4-oxo-butanoic acid derivative is provided for use as a kynurenine-3-hydroxylase inhibitor.

In particular, the present invention relates to the use of a compound of formula (I), or a pharmaceutically acceptable salt thereof, in the prevention and/or treatment of a neurodegenerative disease wherein the inhibition of the enzyme kynurenine-3-hydroxylase is needed.

More in particular, this invention refers to the use of a compound of formula (I), or a pharmaceutically acceptable salt thereof, in the prevention and/or treatment of a neurodegenerative disease which comprises Huntington's chorea, Alzheimer's disease, dementia caused by acquired immunodeficiency syndrome (AIDS), infarctual dementia, cerebral ischemia, cerebral hypoxia, Parkinson's disease, epilepsy, head and spinal cord injury, amyotrophic lateral sclerosis, glaucoma/retinopathy, infections and inflammations of the brain.

A preferred class of compounds of formula (I) according to the invention are compounds of formula (I), if the case, either as single isomers or as a mixture of isomers, wherein R is hydroxy or —$OR_5$ in which $R_5$ is $C_1$–$C_6$ alkyl;

one of X, Y and Z is hydrogen and the other two are, each independently, hydrogen, halogen, cyano, nitro, $C_1$–$C_6$ alkyl, phenyl, benzyl, $C_2$–$C_4$ alkenyl, $C_2$–$C_4$ alkynyl, $C_1$–$C_6$ alkoxy or $C_1$–$C_6$ alkylthio;

$R_1$, $R_2$, $R_3$ and $R_4$ are, each independently, hydrogen, halogen, hydroxy, thiol, $C_1$–$C_6$ alkoxy, $C_1$–$C_6$ alkylthio, $C_1$–$C_6$ alkyl, phenyl, benzyl or $C_2$–$C_4$ alkenyl, or $R_1$ and $R_3$ or $R_2$ and $R_4$ together form a group =$CHR_8$ in which $R_8$ is hydrogen, a straight $C_1$–$C_5$ alkyl chain or phenyl; and the pharmaceutically acceptable salts thereof.

Examples of compounds of formula (I) either as single enantiomer or as mixture of enantiomers, are listed below:

4-(3'-chlorophenyl)-4-oxo-butanoic acid;
4-(3'-fluorophenyl)-4-oxo-butanoic acid;
4-(3'-bromophenyl)-4-oxo-butanoic acid;
4-(3'-nitrophenyl)-4-oxo-butanoic acid;
4-(3',4'-dichlorophenyl)-4-oxo-butanoic acid;
Methyl 4-(3',4'-dichlorophenyl)-4-oxo-butanoate;
4-(3',4'-difluorophenyl)-4-oxo-butanoic acid;
4-(3'-nitro-4'-fluorophenyl)-4-oxo-butanoic acid;
4-(3'-nitro-4'-chlorophenyl)-4-oxo-butanoic acid;
4-(3'-nitro-4'-methoxyphenyl)-4-oxo-butanoic acid;
2-hydroxy-4-(3'-bromophenyl)-4-oxo-butanoic acid;
2-hydroxy-4-(3'-chlorophenyl)-4-oxo-butanoic acid;
2-hydroxy-4-(3'-fluorophenyl)-4-oxo-butanoic acid;
2-hydroxy-4-(3'-nitrophenyl)-4-oxo-butanoic acid;
2-hydroxy-4-(3',4'-dichlorophenyl)-4-oxo-butanoic acid;
Methyl 2-hydroxy-4-(3',4'-dichlorophenyl)-4-oxo-butanoate;
2-methoxy-4-(3'-bromophenyl)-4-oxo-butanoic acid;
2-methoxy-4-(3',4'-dichlorophenyl)-4-oxo-butanoic acid;
2-methyl-4-(3'-fluorophenyl)-4-oxo-butanoic acid;
2-methyl-4-(3'-chlorophenyl)-4-oxo-butanoic acid;
2-methyl-4-(3'-nitrophenyl)-4-oxo-butanoic acid;

and their pharmaceutically acceptable salts.

The present invention also refers to a selected class of 4-phenyl-4-oxo-butanoic acid derivatives of formula (I), as novel compounds.

The present invention therefore provide a 4-phenyl-4-oxo-butanoic acid derivative of formula (IA) either as single isomer or as a mixture of isomers

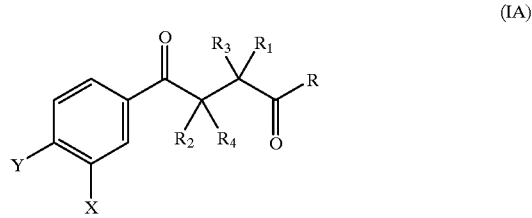

(IA)

wherein
X and Y are, each independently, fluorine or chlorine;
R is hydroxy; —$OR_5$ in which $R_5$ is $C_1$–$C_6$ alkyl, phenyl, benzyl, $C_2$–$C_4$ alkenyl or $C_2$–$C_4$ alkynyl; —$N(R_6)_2$ or —$N(R_6)OR_6$ in which each of $R_6$ is hydrogen, $C_1$–$C_6$ alkyl, $C_2$–$C_4$ alkenyl, $C_2$–$C_4$ alkynyl, phenyl or benzyl;
$R_1$, $R_2$, $R_3$ and $R_4$ are, each independently, hydrogen, halogen, hydroxy, cyano, thiol, $C_1$–$C_6$ alkoxy, $C_1$–$C_6$ alkylthio, $C_1$–$C_6$ alkyl, $C_2$–$C_4$ alkenyl, phenyl or benzyl, or
$R_1$ and $R_3$ or $R_2$ and $R_4$ together form a group =$CHR_8$ in which $R_8$ is hydrogen, a straight $C_1$–$C_5$ alkyl chain or phenyl;
provided that:
(i) when X and Y are both chlorine and $R_1$, $R_2$ and $R_4$ are simultaneously hydrogen, $R_3$ is different from hydrogen, hydroxy, methoxy, ethylthio or isopropylthio; and
(ii) when X and Y are both fluorine, $R_1$, $R_2$, $R_3$ and $R_4$ are not simultaneously hydrogen.

This invention also comprises the pharmaceutically acceptable salts of the compounds of formula (IA) as well as all the possible isomers included in formula (IA), both separately and in mixture.

With reference to both formulae (I) and (IA), the meaning of the various substituents are as follows.

If not otherwise stated, the alkyl, alkoxy and alkylthio chains may be branched or straight chains.

Representative examples of $C_1$–$C_6$ alkyl chains include $C_1$–$C_4$ alkyl chains such as methyl, ethyl, n- and iso-propyl, n-, iso-, sec- and tert-butyl.

Representative examples of $C_1$–$C_6$ alkoxy groups include $C_1$–$C_4$ alkoxy groups such as methoxy and ethoxy.

Representative examples of $C_1$–$C_6$ alkylthio groups include $C_1$–$C_4$ alkylthio groups such as methylthio, ethyltio and isopropylthio.

A halogen atom is fluoro, bromo, chloro or iodo; in particular it is fluoro or chloro. Representative examples of $C_2$–$C_4$ alkenyl group include vinyl and allyl.

Representative examples of $C_2$–$C_4$ alkynyl include ethynyl or propargyl.

The compounds of formula (I) or (IA) may have asymmetric carbon atoms and, for this reason, they can exist either as diastereomeric mixtures or as pure diastereoisomers. Moreover, the compounds of formula (I) and (IA), where an asymmetric centre is present, can exist either as a mixture of optical isomers (enantiomeric mixture) or as single optical isomer (enantiomers).

The present invention therefore include within its scope all the possible isomers and their mixtures and, in addition, both the metabolites and the pharmaceutically acceptable bioprecursors (otherwise known as pro-drugs) of the compounds of formula (I) and (IA).

The pharmaceutically acceptable salts of the compounds of formula (I) and (IA) include the salts of inorganic bases, for example hydroxides of alkali metals, e.g. sodium or potassium, or alkaline-heart metals, e.g. calcium or magnesium, and the salts of organic bases, such as, e.g., aliphatic amines, e.g. methyl amine, ethyl amine or diethyl amine, or heterocyclic amines, e.g. piperidine.

A particular class of compounds of formula (IA) according to the invention are compounds of formula (IA), if the case, either as single isomers or as mixture of isomers, wherein X and Y are, each independently, fluorine or chlorine;
R is hydroxy or —$OR_5$ in which $R_5$ is $C_1$–$C_6$ alkyl;
$R_1$, $R_2$, $R_3$ and $R_4$ are, each independently, hydrogen, halogen, cyano, hydroxy, thiol, $C_1$–$C_6$ alkoxy, $C_1$–$C_6$ alkylthio, $C_1$–$C_6$ alkyl, phenyl, benzyl or $C_2$–$C_4$ alkenyl, or
$R_1$ and $R_3$ or $R_2$ and $R_4$ together form a group =$CHR_8$ in which $R_8$ is hydrogen, a straight $C_1$–$C_5$ alkyl or phenyl;

and the pharmaceutically acceptable salts thereof;
provided that:
(i) when X and Y are both chlorine and $R_1$, $R_2$ and $R_4$ are simultaneously hydrogen, $R_3$ is different from hydrogen, hydroxy, methoxy, ethylthio or isopropylthio; and
(ii) when X and Y are both fluorine, $R_1$, $R_2$, $R_3$ and $R_4$ are not simultaneously hydrogen.

Specific examples of preferred compounds of formula (IA), either as single isomers or as mixture of isomers, are listed below:

2-hydroxy-4-(3',4'-difluorophenyl)-4-oxo-butanoic acid;
2-methoxy-4-(3',4'-difluorophenyl)-4-oxo-butanoic acid;
2-hydroxy-3-methyl-4-(3',4'-dichlorophenyl)-4-oxo-butanoic acid;
2-hydroxy-3-phenyl-4-(3',4'-dichlorophenyl)-4-oxo-butanoic acid;
2-hydroxy-3-benzyl-4-(3',4'-dichlorophenyl)-4-oxo-butanoic acid;
2-methyl-4-(3',4'-dichlorophenyl)-4-oxo-butanoic acid;
2-methyl-4-(3',4'-difluororophenyl)-4-oxo-butanoic acid;
2-chloro-4-(3',4'-dichlorophenyl)-4-oxo-butanoic acid;
2-chloro-4-(3',4'-difluorophenyl)-4-oxo-butanoic acid;
2-fluoro-4-(3',4'-dichlorophenyl)-4-oxo-butanoic acid;
2-fluoro-4-(3',4'-difluorophenyl)-4-oxo-butanoic acid;
2-thiomethyl-4-(3',4'-dichlorophenyl)-4-oxo-butanoic acid;
2-methyliden-4-(3',4'-dichlorophenyl)-4-oxo-butanoic acid;
2-phenyl-4-(3',4'-dichlorophenyl)-4-oxo-butanoic acid;
2-benzyl-4-(3',4'-dichlorophenyl)-4-oxo-butanoic acid;
3-methyl-4-(3',4'-dichlorophenyl)-4-oxo-butanoic acid;
3-methyl-4-(3',4'-dichlorophenyl)-4-oxo-butanoic acid;
3-phenyl-4-(3',4'-dichlorophenyl)-4-oxo-butanoic acid;
3-benzyl-4-(3',4'-dichlorophenyl)-4-oxo-butanoic acid;
(R,S)-methyl-2-hydroxy-4-(3',4'-dichlorophenyl)-4-oxo-butanoate;
(R,S)-methyl-2-benzyl-4-(3',4'-dichlorophenyl)-4-oxo-butanoate;

and their pharmaceutically acceptable salts.

The present invention also provides a compound of formula (IA) for use in a method of treating the human or animal body by therapy.

Typically, a compound of formula (IA) is provided for use as a kynurenine-3-hydroxylase inhibitor.

The compounds of formula (I) or (IA) may be prepared by a process which comprises:

a) reacting a compound of formula (II)

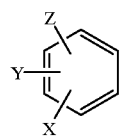

(II)

wherein
X, Y and Z are, each independently, hydrogen, halogen, cyano, $C_1$–$C_6$ alkyl, phenyl, benzyl, $C_2$–$C_4$ alkenyl, $C_2$–$C_4$ alkynyl, $C_1$–$C_6$ alkoxy or $C_1$–$C_6$ alkylthio;
with a compound of formula (III)

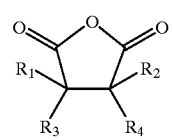

(III)

wherein
$R_1$, $R_2$, $R_3$ and $R_4$ are each independently, hydrogen, $C_1$–$C_6$ alkyl, $C_2$–$C_4$ alkenyl, phenyl or benzyl, or
$R_1$ and $R_3$ or $R_2$ and $R_4$ together form a group =$CHR_8$ in which $R_8$ is hydrogen, a straight $C_1$–$C_5$ alkyl chain or phenyl; so obtaining a compound of formula (I) or (IA) wherein
X, Y, Z, $R_1$, $R_2$, $R_3$ and $R_4$ are as defined above and R is hydroxy; or b) reacting a compound of formula (IV)

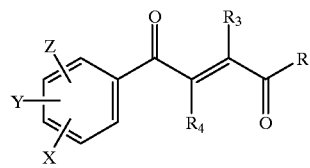

(IV)

wherein
X, Y and Z are, each independently, hydrogen, halogen, cyano, nitro, $C_1$–$C_6$ alkyl, phenyl, benzyl, $C_2$–$C_4$ alkenyl, $C_2$–$C_4$ alkynyl, $C_1$–$C_6$ alkoxy or $C_1$–$C_6$ alkylthio;
R is hydroxy or —$OR_5$ in which $R_5$ is $C_1$–$C_6$ alkyl; and
$R_3$ and $R_4$ are, each independently, hydrogen, halogen, $C_1$–$C_6$ alkyl, phenyl or benzyl;
with a compound of formula (V)

$R_1$—$R_2$  (V)

wherein
$R_1$ is hydrogen, halogen, hydroxy, sulfidryl $C_1$–$C_6$ alkoxy, $C_1$–$C_6$ alkylthio, $C_1$–$C_6$ alkyl, phenyl or benzyl; and
$R_2$ is hydrogen, halogen, hydroxy, an alkali metal, e.g. lithium or an alkaline-earth metal, e.g. magnesium; provided that when $R_1$ is sulfidryl or $C_1$–$C_6$ alkylthio $R_2$ is not hydroxy or halogen;
so obtaining a compound of formula (I) or (IA) wherein
X, Y, Z, $R_1$, $R_2$, $R_3$ and $R_4$ are as defined above;
and, if desired, c) converting a compound of formula (I) or (IA) as obtained in step a) or b) above, into another compound of formula (I) or (IA) in which one or more of $R_1$, $R_2$, $R_3$ and $R_4$ has/have different meaning; and/or, if desired, d) converting a compound of formula (I) or (IA) as obtained in step a), b) or c) above, into another compound of formula (I) or (IA) wherein R is not hydroxy; or, if desired, e) converting a compound of formula (I) or (IA) as obtained in step a), b) or c) above, into a pharmaceutically acceptable salt thereof or obtaining the free compound from the corresponding salt; and/or, if the compound of formula (I) or (IA) is obtained as a mixture of isomers, f) obtaining a single isomer of a compound of formula (I) or (IA) as obtained in step a), b), c), d) or e) from the corresponding mixture of isomers.

The reaction of a compound of formula (II) with a compound of formula (III), described as step a), can be carried out according to known methods; for example, following the procedures reported in: Somerville L. F., Organic Synthesis, Collect. Vol. 2, 81, (1943); Child R. G., Arzneim.-Forsch./Drug Res., 30, 695–702, (1980); Quallich G. J., J.Org.Chem., 55, 4971–4973 (1990); Thyes M., J.Med.Chem., 26, 800–807(1983); Hester J. B., J.Med.Chem., 34, 308–315 (1991); and De Saqui-Sannes, Pharm.Acta Helv., 66, 7, 189–192 (1991).

For example, this reaction can be performed in the presence of a suitable Lewis acid catalyst, in an inert solvent such as, e.g., dichloromethane or 1,2-dichloroethane, or in an appropriate aromatic hydrocarbon such as, e.g., chlorobenzene, nitrobenzene or in an excess of a compound of formula (II) itself; at a temperature ranging from about −10° C. to about 100° C.; optionally in the presence of a co-solvent, e.g. nitromethane.

A suitable Lewis acid may be, e.g., anhydrous aluminium trichloride, anhydrous tin dichloride, titanium tetrachloride or anhydrous zinc dichloride; typically, anhydrous aluminium trichloride.

The compounds of formula (II) are known compounds.

The compounds of formula (III) are known compounds or can be prepared by known procedures from known compounds.

The reaction of a compound of formula (IV) with a compound of formula (V), described as step b), may be carried out according to known methods: see, for example, Kazuya Kameo, Chem. Pharm. Bull., 36, 6, 2050–2060, (1988) and E. Buchia, Chem. Ber. 82, 63 (1949).

A compound of formula (V) may also be in the form of a salt with an alkali metal ion such as, e.g, sodium, lithium or potassium ion, preferably lithium or sodium; in this case, the compounds of formula (V) may be, e.g., sodium hydroxyde, sodium disulfide, sodium $C_1$–$C_6$ alkoxyde or sodium $C_1$–$C_6$ thiolate.

For example, this reaction can be carried out in an inert solvent, e.g., dioxane, tetrahydrofuran, ethyl ether, or in a solvent acting as a proton donor, e.g., water, methanol, ethanol, or in an excess of a compound of formula (V) itself, at a temperature ranging from about −50° C. to the reflux temperature.

A compound of formula (V) may also be in the form of an organometallic reagent, e.g, phenyl-lithium, methyl-lithium, phenylmagnesium bromide or methyl magnesium bromide; in this case $R_2$ is, e.g., lithium or an alkaline earth-metal.

The reaction of a compound of formula (IV) with a compound of formula (V), when the compound of formula (V) is an organometallic reagent, may be carried out according to known methods; see, for example, E. Erdik, Tetrahedron, 40, 641–657 (1984); S. Cacchi, A. Arcadi, J.Org.Chem., 48, 4236–4240 (1983); C. A. Ibarra, J.Chem.Soc.P.T.II, 467–470 (1991); G. Quinkert, Angew.Chem. Int. Ed. Engl., 25, 992–998 (1996); J. Leonard, M. F. Jones, Synlett, 9, 741–742 (1992); B. Lipshutz, Tetrahedron Lett., 34, 6689–6692 (1993); J. L. Leuche, J.Org.Chem., 48, 3837–3846 1983); M. Martinelli, J. Peterson, Tetrahedron Lett., 31, 5401–5404 (1990); and T. Watanabe, Synlett, 3, 175–177 (1994). For example, this reaction can be carried out in an inert solvent, e.g., dioxane, tetrahydrofuran or ethyl ether, at a temperature ranging from about −78° C. to room temperature, optionally in the presence of a transition metal catalyst.

The compounds of formula (V) are known compounds or may be prepared from known compounds according to known methods.

The compounds of formula (IV) are either known compounds or can be obtained by known methods from known compounds. For example, a compound of formula (IV) can be obtained following the process outlined in Scheme 3 below, namely, reacting a compound of formula (II) with a compound of formula (VI).

Scheme 3

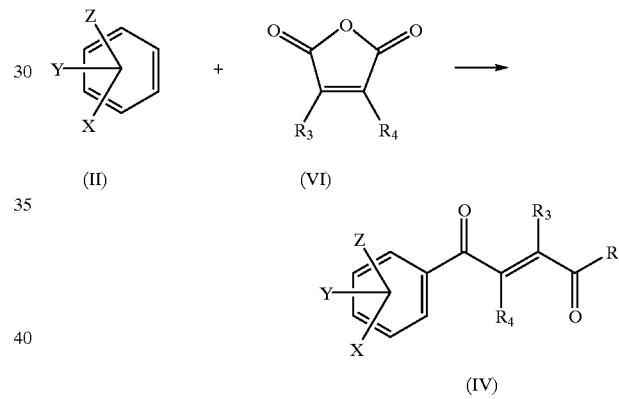

In the above Scheme 3

X, Y, and Z are, each independently, hydrogen, halogen, cyano, $C_1$–$C_6$ alkyl, phenyl, benzyl, $C_2$–$C_4$ alkenyl, $C_2$–$C_4$ alkynyl, $C_1$–$C_6$ alkoxy or $C_1$–$C_6$ alkylthio;

$R_3$ and $R_4$ are, each independently, hydrogen, $C_1$–$C_6$ alkyl, phenyl or benzyl; and R is hydroxy.

In a compound of formula (IV), obtained as described in Scheme 3, R is hydroxy, namely it contains a free carboxy group; such a compound can be converted into another compound of formula (IV) in which R is not hydroxy according to known methods.

The reaction of a compound of formula (II) with a compound of formula (VI), as decribed in Scheme 3, can be carried out according to known methods (Kazuya Kameo, Chem. Pharm. Bull., 36 (6), 2050–2060 (1988); and Bianchi M., Eur. J. Med. Chem., 23, 45–52 (1988).

For example, the reaction can be performed in the presence of a suitable Lewis acid catalyst, in an inert solvent such as, e.g., dichloromethane or 1,2-dichloroethane, or in a appropriate aromatic hydrocarbon such as, e.g., chlorobenzene or nitrobenzene, or in an excess of a compound of formula(II) itself; at a temperature ranging from about −10°

C. to about 100° C.; optionally in the presence of a co-solvent, e.g. nitromethane.

A suitable Lewis acid may be anhydrous aluminium trichloride, anhydrous tin dichloride, titanium tetrachloride or anhydrous zinc dichloride; typically, anhydrous aluminium trichloride.

The compounds of formula (II) are known compounds.

The compounds of formula (VI) are known compounds or can be prepared by known procedures from known compounds.

In alternative, the compounds of formula (IV) can be prepared following the procedure as outlined in Scheme 4 below; namely, reacting a compound of formula (VII) with a compound of formula (VIII).

Scheme 4

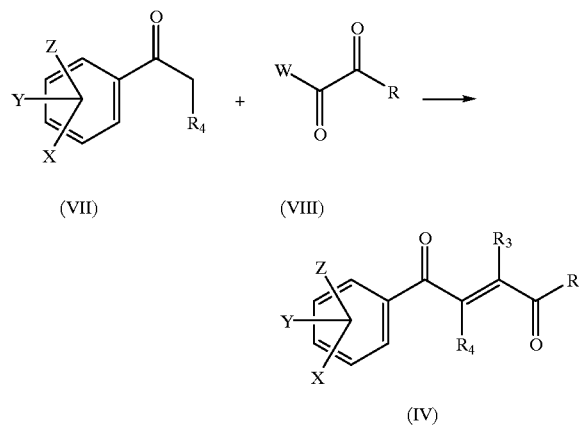

(VII)  (VIII)

(IV)

In the above Scheme 4

X, Y, and Z are as defined in Scheme 3;

$R_4$ is hydrogen, $C_1$–$C_6$ alkyl, phenyl or benzyl;

$R_3$ is hydrogen, $C_1$–$C_6$ alkyl, phenyl or benzyl;

R is hydroxy or —$OR_5$ in which $R_5$ is $C_1$–$C_6$-alkyl; and

W is hydrogen, hydroxy, $C_1$–$C_6$ alkyl, phenyl, benzyl or $C_1$–$C_6$ alkoxy.

A compound obtained as described in Scheme 4, containing a free carboxy group, namely a compound of formula (IV) in which R is hydroxy, can be converted into another compound of formula (IV) in which R is not hydroxy according to known methods.

The reaction of a compound of formula (VII) with a compound of formula (VIII), as decribed in Scheme 4, can be carried out according to known methods; see, e.g., Witiak M., J. Med. Chem., 14, 8, 758–766 (1971); Williams H. W. R., J. Med. Chem., 26, 1196–1200 (1983); and C. G. Wermuth, G. Leclerc, P. Melounou, Chim.Ther.,141–145 (1971).

For example, the reaction can be performed either using a suitable acid or basic catalyst, e.g., hydrochloric acid, sulforic acid, potassium hydroxyde, sodium methoxyde or without catalyst, in a solvent such as, e.g., glacial acetic acid, dioxane, toluene or benzene, or in an excess of the compound of formula (VII) itself, at a temperature ranging from about −10° C. to about 120° C.

The compounds of formula (VII) are either known compounds or can be obtained from known compounds according to procedures well known in the art.

The compounds of formula (VIII) are either known compounds or can be prepared according to well known procedures.

The conversion of a compound of formula (I) or (IA) into another compound of formula (I) or (IA) in which one or more of $R_1$, $R_2$, $R_3$ and $R_4$ has/have different meaning, described as step c), may be carried out following known procedures.

For example, a compound of formula (I) or (IA) wherein $R_2$ and/or $R_4$ are/is hydrogen can be converted into another compound of formula (I) or (IA) wherein $R_2$ and/or $R_4$ substituent/s are/is $C_1$–$C_6$ alkyl or benzyl, by means of well known procedures of ketones+alkylation, e.g. enamine or enol ethers alkylation methods, see, e.g., Carruthers, Some modern methods of organic synthesis, Cambridge University Press (1980).

A compound of formula (I) or (IA) wherein $R_2$ and/or $R_4$ are/is hydrogen, can be converted into another compound of formula (I) or (IA) wherein $R_2$ and/or $R_4$ are/is halogen by means of well known procedures of ketones enolates halogenation.

A compound of formula (I) or (IA) wherein $R_2$ and/or $R_4$ are/is hydrogen, can be converted into another compound of formula (I) or (IA) wherein $R_2$ and/or $R_4$ are/is hydroxy by known methods, see, e.g., Hassner's α-hydroxylation of ketones, Tetrahedron Letters, 1283–86 (1981); ibid., 4319–22 (1974); and J.Org.Chem., 40, 3427–29 (1975).

A compound of formula (I) or (IA) wherein $R_1$ and/or $R_3$ are/is hydrogen and $R_2$, and/or $R_4$ are not simultaneously hydrogen and R is —$OR_5$ in which $R_5$ is $C_1$–$C_6$ alkyl, can be converted into another compound of formula (I) or (IA) wherein of the $R_1$ and/or $R_2$ are/is $C_1$–$C_6$ alkyl or benzyl, by means of well known procedures of esters enolate alkylation.

A compound of formula (I) or (IA) which contains a free carboxy group, namely a compound of formula (I) or (IA) in which R is hydroxy, can be converted into another compound of formula (I) or (IA) in which R is not hydroxy.

For example, a compound of formula (I) or (IA) wherein R is hydroxy, can be converted into another compound of formula (I) or (IA) wherein R is —$OR_5$ in which $R_5$ is as defined above, by usual esterification methods; for example, following the procedure described in: E. Haslam, Tetrahedron, 36, 2409–2433 (1980). Preferably, such an esterification reaction can be carried out via a reactive intermediate of the carboxylic acid, which may be isolated or not, by reaction with the appropriate alcohol of formula $R_5OH$ in which $R_5$ is as defined above. The reaction can be carried out in a customary solvent, e.g. dichloromethane, tetrahydrofuran, toluene, or in the presence of an excess of the alcohol itself of formula $R_5OH$, at a temperature which may range from about −20° C. to about 50° C. Intermediate reactive derivatives of the carboxylic acid may be, for example, acid halides, e.g. chloride, mixed anhydrides, e.g. etoxycarbonyl or tert-butyloxy anhydride, or a suitable reactive intermediate obtained "in situ", for example, by reaction with, e.g., dicychloexylcarbodiimide or carbonyl diimidazole.

The esterification reaction may be also carried out by treatment of a compound of formula (I) or (IA) in which R is hydroxy, with a suitable alkylating agent of formula $R_5$-X in which $R_5$ is as defined above, and X is an appropriate leaving group such as, e.g., a halogen atom, preferably iodine, or a sulfate ester, in the presence of an inorganic base, e.g. potassium carbonate or bicarbonate, or in the presence of an organic base, e.g. diazabicycloundecene (DBU), in a suitable solvent, e.g. dimethylformamide, at a reaction temperature that may range from about 0° C. to about 60° C.

Furthermore, a compound of formula (I) or (IA) wherein R is hydroxy, can be converted into a corresponding compound of formula (I) or (IA) wherein R is —N($R_6$)$_2$ or —NOR$_6$, wherein $R_6$ is as defined above, according to known methods; preferably, via an intermediate reactive derivative thereof, which can be isolated or not. Intermediate derivatives may be active esters, e.g., $NO_2$-phenyl esters or N-hydroxysuccinimide esters, acid halides, preferably chlorides, mixed anhydrides, e.g. ethoxycarbonyl or tert-butyloxycarbonyl anhydrides, or reactive intermediates obtained "in situ" by reaction of the acid with carbonyl diimidazole.

For example, a reactive intermediate as defined above, which can be obtained following conventional ways (for example, those usually employed in the synthesis of peptides), is reacted with ammonia or an appropriate amine HN($R_6$)$_2$ or an appropriate hydroxylamine or protected hydroxylamine of formula HNO-$R_7$ wherein $R_7$ is a suitable $C_1$–$C_6$ alkyl or benzyl substituent or protecting group; in this last case, $R_7$ is preferably a benzyl or trialkyl-silyl group. The reaction solvent may be a customary solvent, such as e.g., dichloromethane, tetrahydrofuran, dioxane or an excess of the amine itself, and the reaction temperature may range from about $-20°$ C. to about $50°$ C.

The carbonyl group present in the compound of formula (I) or (IA) may be optionally protected during the above described reactions of transformation of a compound of formula (I) or (IA) into another compound of formula (I) or (IA). The carbonyl protection may be carried out using the techniques of carbonyl protection well known in the art, e.g., H. Meerwein, in: Houben-Weyl, Methoden der Organischen Chemie, Vol.VI/4, Geroge Thieme Verlag, p.222 (1965). The removal of the carbonyl protecting group at the end of the transformation may be carried out with usual methods, e.g., M. E. Jung, Tetrahedron Lett., 48, 4175–4178 (1977); R. Sterzycki, Synthesis, 24–725 (1979); G. Baleme, 48, 3336–3338 (1983); and B. H. Lipshutz, Synthetic communications, 12, 267–277 (1982).

The optional salification of a compound of formula (I) or (IA) as well as the conversion of a salt into the corresponding free compound and the separation of a mixture of isomers into the single isomer, may be carried out by usual methods. For example, the separation of a mixture of regioisomers or diastereoisomers into the single isomer may be carried out by conventional methods. Particularly, the separation of regioisomers or diastereoisomers may be carried out by fractional crystallization from a suitable solvent or by chromatography, either flash column chromatography or high pressure liquid chromatography.

As previously described, some of the compounds of formula (I) or (IA) may exist as enantiomers; where enantiomers of compounds of formula (I) or (IA) are possible, the separation of the racemic compounds of formula (I) or (IA) into the corresponding pure enantiomers can be carried out according to techniques and procedures well known in the art; for example, either high pressure liquid chromatography on a chiral stationary phase, or resolution via diastereoisomeric salt formation of a compound of formula (I) or (IA) where R is hydroxy, with a suitable optically active organic base, e.g. phenylethylamine, ephedrine or brucine, and subsequent separation of the pure diastereoisomeric salt by selective recrystallization.

As already said, the compounds of formula (IA) represent a selected class of compounds of formula (I) and are thus effective in the prevention and/or treatment of all the disease for which the compounds of formula (I) have been indicated as therapeutic agents.

Accordingly, the compound of formula (IA) are useful as kynurenine-3-hydroxylase inhibitors; in particular, they are useful in the prevention and/or treatment of a neurodegenerative disease wherein the inhibition of the enzyme kynurenine-3-hydroxylase is needed.

More in particular, the compounds of formula (IA) can be useful in the prevention and/or treatment of a neurodegenerative disease which comprises: Huntington's chorea, Alzheimer's disease, dementia caused by acquired immunodeficiency syndrome (AIDS), infarctual dementia, cerebral ischemia, cerebral hypoxia, Parkinson's disease, epilepsy, head and spinal cord injury, amyotrophic lateral sclerosis, glaucoma/retinopathy, infections and inflammation of the brain.

A human or animal may thus be treated by a method which comprises the administration of a pharmaceutically effective amount of a compound of formula (I) or (IA) or salt thereof.

The efficacy of the compounds of formula (I) or (IA) in the inhibition of the enzyme kynurenine-3-hydroxylase has been evaluated both in rat brain homogenate and in rat liver homogenate, determining the conversion of L-kynurenine to L-3-hydroxy-kynurenine according to the methods described below.

Kynurenine-3-hydroxylase Assay in the Rat Brain

Brain was homogenized in ice-cold 0.32 M sucrose and centrifuged at 12000×g for 30 min at $4°$ C. The pellet was washed three times with 0.32 M sucrose by centrifugation and suspended in 0.14 M KCl in 20 mM K-phosphate buffer at pH 7 (1 g tissue in 2 ml buffer).

The reaction mixture contained: 75 $\mu$l of suspended homogenate; 100 $\mu$l of substrate solution containing 50 mM K-phosphate buffer pH 7.5, 2 mM $MgCl_2$, 0.4 mM NADPH, 50 $\mu$M L-kynurenine (final concentration), and 25 $\mu$l of different concentrations of inhibitor solutions. The reaction was stopped by addition of 200 $\mu$l of 1 M $HClO_4$ after 60 min incubation. L-3-hydroxykynurenine formed was quantified by HPLC with coulometric detection at a working voltage of +0.2 V. The column was a 10 cm $C_{18}$ reversed phase (3 $\mu$m. The mobile phase consisted of 950 ml distilled water, 20 ml acetonitrile, 9 ml triethylamine, 5.9 ml phosphoric acid, 100 mg sodium EDTA and 1.5 g heptanesulfonic acid. The flow rate was 1 ml/min.

Kynurenine-3-hydroxylase Assay in the Rat Liver

The efficacy of the compounds of the present invention in the inhibition of the enzyme kynurenine-3-hydroxylase has been evaluated in rat liver mitochondrial extract as reported below, according to known methods (A Radiometric Assay for Kynurenine 3-Hydroxylase Based on the Release of $^3H_2O$ during Hydroxylation of L-(3,5-$^3$H)Kynurenine; Joel B. Erickson, Ellen M. Flanagan, Suzanne Russo, and John F. Reinhard. Jr.; Analytical Biochem. (1992), 205, 257–262) with minor modifications.

The assay for kynurenine 3-hydroxylase was based on the enzymatic synthesis of tritiated water during the hydroxylation reaction. Radiolabeled water was quantified following selective adsorption of the isotopic substrate and its metabolite with activated charcoal.

Rat liver mitochondrial extract was used as enzymatic preparation for this assay.

The assay for kynurenine 3-hydroxylase activity was carried out at $37°$ C. for a time of 30 min. The reaction mixture of a total volume of 100 ml was constituted of 44 mg of suspended extract, 100 mM Tris/Cl$^-$ buffer pH 8.1, 10 mM EDTA, 100 mM Kcl, 0.8 mM NADPH, 0.025 mM L-kynurenine, 0.5 mCi L-(3,5-$^3$H)Kynurenine (10 Ci/mmol) and 10 ml of different concentration of inhibitor solutions. After the incubation the reaction was terminated by the addition of 1 mL of 7.5% (w/v) activated charcoal, vortexed and centrifugated for 7 min.

A 500 ml aliquot of supernatant was counted by scintillation spectroscopy in 5 ml of liquid scintillation.

As an example, the compounds of the present invention:

4-(3',4'-dichlorophenyl)-4-oxo-butanoic acid, (internal code: PNU 156588);
4-(3',4'-difluorophenyl)-4-oxo-butanoic acid (internal code: PNU 157720);
Methyl 4-(3',4'-dichlorophenyl)-4-oxo-butanoate (internal code: PNU 158381);
(R,S)-2-hydroxy-4-(3'-chlorophenyl)-4-oxo-butanoic acid (internal code: PNU 158789);
(R,S)-2-hydroxy-4-(3'-fluorophenyl)-4-oxo-butanoic acid (internal code: PNU 158790);
(R,S)-2-hydroxy-4-(3'-nitrophenyl)-4-oxo-butanoic acid (internal code: PNU 158791);
(R,S)-2-hydroxy-4-(3',4'-dichlorophenyl)-4-oxo-butanoic acid (internal code: PNU 157695)
(S)-2-hydroxy-4-(3',4'-dichlorophenyl)-4-oxo-butanoic acid (internal code: PNU 161176);
(R)-2-hydroxy-4-(3',4'-dichlorophenyl)-4-oxo-butanoic acid (internal code: PNU 161210);
Methyl(R,S)-2-hydroxy-4-(3',4'-dichlorophenyl)-4-oxo-butanoate (internal code: PNU 161211)
(R,S)-2-hydroxy-4-(3',4'-difluorophenyl)-4-oxo-butanoic acid (internal code: PNU 158783);
(R,S)-2-methoxy-4-(3',4'-difluorophenyl)-4-oxo-butanoic acid (internal code: PNU 158380);
(R,S)-2-methoxy-4-(3'-4'-dichlorophenyl)-4-oxobutanoic acid (internal code: PNU 157960);
(R,S)-2-methyl-4-(3',4'-dichlorophenyl)-4-oxo-butanoic acid (internal code: PNU 157718);
(R,S)-3-methyl-4-(3',4'-dichlorophenyl)-4-oxo-butanoic acid (internal code: PNU 161243);
2-hydroxy-3-benzyl-4-(3',4'-dichlorophenyl)-4-oxo-butanoic acid (PNU 167536);
(R,S)-2-methyl-4-(3',4'-difluorophenyl)-4-oxo-butanoic acid (internal code: PNU 157952);
(R,S)-2-chloro-4-(3',4'-dichlorophenyl)-4-oxo-butanoic acid (internal code: PNU 158781);
2-methyliden-4-(3',4'-dichlorophenyl)-4-oxo-butanoic acid (internal code: PNU 158432);
(R,S)-3-phenyl-4-(3',4'-dichlorophenyl)-4-oxo-butanoic acid (internal code: PNU 167541);
(R,S)-Methyl-2-benzyl-4-(3',4'-dichlorophenyl)-4-oxo-butanoate (internal code: PNU 167531);
(R,S)-2-phenyl-4-(3',4'-dichlorophenyl)-4-oxo-butanoic acid(internal code: PNU 167533); and
(R,S)-2-benzyl-4-(3',4'-dichlorophenyl)-4-oxo-butanoic acid (internal code: PNU 167532);

have been tested according to the methods described above.

The obtained results, are reported in the following Table1.

TABLE 1

| Compound | IC$_{50}$ ($\mu$M) (Brain) | IC$_{50}$ ($\mu$M) (Liver) |
| --- | --- | --- |
| PNU 156588 | 0.9 | 3.9 |
| PNU 157720 | 3.7 | 18.3 |
| PNU 158381 | — | 5.7 |
| PNU 158789 | 0.45 | 1.8 |
| PNU 158790 | 5.6 | 11.5 |
| PNU 158791 | 1.95 | 11.2 |
| PNU 157695 | 0.3 | 1.4 |
| PNU 161176 | 0.28 | 0.42 |
| PNU 161210 | 6.7 | 14.4 |
| PNU 161211 | 3.1 | 5.6 |

TABLE 1-continued

| Compound | IC$_{50}$ ($\mu$M) (Brain) | IC$_{50}$ ($\mu$M) (Liver) |
| --- | --- | --- |
| PNU 158783 | 1.45 | 2.8 |
| PNU 158380 | 12.6 | 42.4 |
| PNU 157960 | 1.2 | 6.9 |
| PNU 157718 | 3.5 | 6.9 |
| PNU 161243 | 14.3 | — |
| PNU 167536 | — | 61.6 |
| PNU 157952 | 3.9 | 55.1 |
| PNU 158781 | 2.2 | 13.3 |
| PNU 158432 | — | 36 |
| PNU 167541 | — | 55.0 |
| PNU 167531 | — | 1.9 |
| PNU 167533 | — | 19.5 |
| PNU 167532 | — | 0.8 |

The tested compounds were found to be significantly active in inhibiting the enzyme kynurenine-3-hydroxylase.

The compounds of the invention can be administered in a variety of dosage forms, e.g. orally, in the form of tablets, capsules, sugar or film coated tablets, liquid solutions or suspensions; parenterally, e.g. intramuscolarly or by intravenous injection or infusion.

The dosage level suitable for administration to adult humans depends on the age, weight, conditions of the patient and on the administration route; for example, the dosage adopted for oral administration for the compounds of the invention may range from about 10 to about 500 mg pro dose, from 1 to 5 times daily.

The present invention also provides pharmaceutical compositions comprising a compound of formula (I) or (IA) as an active ingredient in association with a pharmaceutically acceptable excipient (which can be a carrier or a diluent).

Furthermore, the present invention provides pharmaceutical compositions comprising a compound of formula (I) as an active ingredient in association with a pharmaceutically acceptable excipient (which can be a carrier or a diluent) for use as kynurenine 3-hydroxylase inhibitor.

The pharmaceutical compositions containing the compounds of the invention are usually prepared following conventional methods and are administered in a pharmaceutically suitable form.

For example, the solid oral forms may contain, together with the active compound, diluents, e.g. lactose, dextrose, saccharose, sucrose, cellulose, corn starch or potato starch; lubricants, e.g. silica, talc, stearic acid, magnesium or calcium stearate, and/or polyethylene glycols; binding agents, e.g. starches, arabic gum, gelatin, methylcellulose, carboxymethylcellulose or polyvinyl pyrrolidone; disaggregating agents, e.g. a starch, alginic acid, alginates or sodium starch glycolate; effervescing mixtures; dyestuffs; sweeteners; wetting agents such as lecithin, polysorbates, laurylsulphates; and, in general, non-toxic and pharmacologically inactive substances used in pharmaceutical formulations. Said pharmaceutical preparations may be manufactured in known manner, for example, by means of mixing, granulating, tabletting, sugar-coating, or film-coating processes.

The liquid dispersions for oral administration may be e.g. syrups, emulsions and suspensions.

The syrups may contain as carrier, for example, saccharose or saccharose with glycerine and/or mannitol and/or sorbitol. The suspensions and the emulsions may contain as carrier, for example, a natural gum, agar, sodium alginate, pectin, methylcellulose, carboxymethylcellulose, or polyvinyl alcohol. The suspension or solutions for intramuscolar injections may contain, together with the active compound, a pharmaceutically acceptable carrier, e.g. sterile water, olive oil, ethyl oleate, glycols, e.g. propylene glycol, and, if desidered, a suitable amount of lidocaine hydrochloride. The solutions for intravenous injections or infusions may contain as carrier, for example, sterile water or preferably they may be in the form of sterile, acqueous, isotonic saline solutions.

The following examples illustrate but do not limit the invention.

EXAMPLE 1

(R,S)-2-methyl-4-(3',4'-dichlorophenyl)-4-oxo-butanoic acid (PNU 157718)

Aluminium chloride anhydrous (2 g, 53 mmol.) was added to a solution of (R,S)-2-methylsuccinic anhydride (2 g, 17 mmol) in dichlorobenzene (16 g , 100 mmol) at ambient temperature. The reaction mixture was heated to 60° C. for 3 hours. and then inverse quenched onto cold water (160 ml), maintaining the temperature below 50° C. After stirring for 15 min., hexane (80 ml) was added and stirring continued for 1.5 hours. The product was filtered and dried in a vacuum oven to give the crude ketoacid as a slightly brown solid, 4.4 g (mp. 98–101° C.). The above crude reaction product was recrystallized from diisopropyl ether to provide 3.5 g (76%) of the pure acid (mp. 119–120° C.), colorless solid.

Calcd. for $C_{11}H_{10}Cl_2O_3$: C, 50.60; H, 3.86; Cl, 27.20

Found: 48.97; 3.94; 26.68

MS, EI: 260.0 (M)$^+$; 173 ($C_6H_3Cl_2CO)^+$.

$^1$H NMR (200 MHz; $d_6$-DMSO), ppm: 1.18 (3H,d); 2.85 (1H, m); 3.08 (1H, dd); 3.40 (1H, dd); 7.78 (1H, d); 7.92 (1H, dd); 8.14 (1H; d).

Analogously, the following compound can be prepared:

2-methyl-4-oxo-4-(3',4'-difluorophenyl)butanoic acid (PNU 157952), colorless needles, mp. 83–85° C.

Calcd. for $C_{11}H_{10}F_2O_3$: C, 57.89; H, 4.42;

Found: 57.78 ; 4.61;

$^1$H NMR (200 MHz; $d_6$-DMSO), ppm: 1.18 (3H d); 2.83(1H, m); 3.10 (1H, dd ); 3.40 (1H, dd); 7.30–7.65 (1H, m ); 7.80–7.90 (1H, m); 7.96–8.08 (1H, m); 12.20 (1H, s).

Analogously, using 2-acetoxysuccinic anhydride, the following compounds can be prepared:

(R,S)-2-hydroxy-4-oxo-4-(3',4'-dichlorophenyl)butanoic acid (PNU 157695); colorless needles, mp. 150–151° C.

Calcd. for $C_{10}H_8Cl_2O_4$: C, 45.67; H, 3.07; Cl, 26.99

Found: 45.41; 3.16; 27.14

MS (EI)m/z: 262 (M)$^+$; 243.9 (M-H$_2$O)$^+$; 217.0 (M-COOH)$^+$; 173 ($C_6H_3Cl_2CO)^+$.

$^1$H NMR (200 MHz; $d_6$-DMSO), ppm: 3.36 (2H, d); 4.42(1H,t); 7.76 (1H, d ); 7.92 (1H, dd); 8.12 (1H, d); 12.20 (1H, bs); (S)-2-hydroxy-4-oxo-(3',4'-dichlorophenyl) butanoic acid (PNU 161176); analogously obtained in 55% yield, using homochiral (S)-2-acetoxysuccinic anhydride: colorless needles, mp. 148–19.5° C., $[\alpha]_D$=–8.55° (EtOH Abs.; c=0.99).

Calcd. for $C_{10}H_8Cl_2O_4$: C, 45.67; H, 3.07; Cl, 26.99

Found: 45.87; 3.23; 26.25; and (R)-2-hydroxy-4-oxo-4-(3',4'-dichlorophenyl)butanoic acid (PNU 161210); analogously obtained in 58% yield, using homochiral (R)-2-acetoxysuccinic anhydride: colorless needles, mp. 150–152° C., $[\alpha]_D$=+8.04° (EtOH Abs.; c=0.97).

Calcd. for $C_{10}H_8Cl_2O_4$: C, 45.67; H, 3.07; Cl, 26.99

Found: 45.73; 3.14; 27.03.

Analogously, using succinic anhydride, the following compounds can be prepared:

4-oxo-4-(3',4'-difluorophenyl)butanoic acid (PNU 157720), m.p. 80–81° C.;

Calcd. for $C_{10}H_8F_2O_3$: C, 56.10; H, 3.32

Found: 56.32; 3.72

MS (EI) m/z: 214.0 (M)$^{.+}$; 141.0 ($C_6H_3F_2CO)^+$.

$^1$H NMR (200 MHz; $d_6$-DMSO), ppm: 2.58 (2H, t); 3.21 (2H, t); 7.53–7.66(1H, m); 7.82–8.04 (2H, m); 12.10 (1H, s); and 4-oxo-4-(3',4'-dichlorophenyl)butanoic acid (PNU 156588), m.p. 166–167° C.

Calcd. for $C_{10}H_8Cl_2O_3$: C, 48.63; H, 3.26; Cl, 28.74

Found: 48.59 ; 3.31 ; 28.35

MS (FAB$^-$) m/z: 245 (M-H)$^-$.

$^1$H NMR (200 MHz; $d_6$-DMSO), ppm: 2.57 (2H, t); 3.23 (2H, t); 7.79 (1H, d); 7.92 (1H, dd); 8.18 (1H, s); 12.10 (1H, broad s).

Analogously, using 2,2-dimethylsuccinic anhydride, the following compound can be prepared:

2,2-dimethyl-4-oxo-4-(3',4'-dichlorophenyl)butanoic acid: light cream plates, m.p. 137–138° C. (diisopropyl ether), Calcd. for $C_{12}H_{12}Cl_2O_3$: C, 52.39; H, 4.40; Cl, 25.77

Found: 52.95; 4.63; 25.22

MS (EI) m/z: 274 (M)$^{.+}$; 188 ($C_6H_3Cl_2COCH_3)^{.+}$; 173 ($C_6H_3Cl_2CO)^{.+}$.

$^1$H NMR (200 MHz; $d_6$-DMSO), ppm: 1.20 (6H,s); 3.35 (2H,s ); 7.78 (1H, d ); 7.90 (1H, dd); 8.16 (1H, s); 12.0 (1H, s).

EXAMPLE 2

2-methyliden-4-oxo-4-(3',4'-dichlorophenyl)butanoic acid (PNU 158432)

Aluminium chloride anhydrous (53 g, 0.13 mol.) was added to a solution of itaconic anhydride (15 g, 0.13 mol.) in dichlorobenzene (100 mL) at room temperature. The reaction mixture was heated to 50° C. for 3 hours. and then inverse quenched with cold water/37% hydrochloric acid (100 mL/100 mL) maintaining the temperature below 30° C. After stirring the quenched reaction for 15 min., hexane (80 mL) was added and stirring continued for 0.5 hours. The product was filtered and dried in a vacuum oven to give the crude unsaturated-ketoacid as a colourless solid, 36 g, recrystallization from diethyl ether provided the pure acid (22 g, 67%) as colourless prisms melting at 156–57° C.

Calcd. for $C_{11}H_8 Cl_2O_3$: C, 51.01; H, 3.11; Cl, 27.41

Found: 51.00; 3.18; 27.00

MS (EI) m/z: 258 (M)$^{.+}$; 173 ($C_6H_3Cl_2CO)^{.+}$.

$^1$H NMR (200 MHz; $d_6$-DMSO), ppm: 4.12 (2H s); 5.68 (1H,s); 6.12 (1H, s); 7.80 (1H,d); 7.96 (1H,dd); 8.18 (1H,d); 12.50 (1H, s).

EXAMPLE 3

(R,S)-2-methoxy-4-oxo-4-(3',4'-difluorophenyl) butanoic acid (PNU 158380)

4-oxo-4-(3',4'-difluorophenyl)-2-butenoic acid (RN: 83844-24-0) was prepared according to Scheme 3 in 55% yield; yellow solid melting at 107–108° C. (toluene), $^1$H-NMR (d$_6$-DMSO) ppm: 6.65 (d, 1H); 7.55–7.64 (m, 1H); 7.83 (d, 1H); 7.85–8.11 (m, 2H); 13.1 (broad s, 1H).

To a solution of 4-oxo-4-(3',4'-difluorophenyl)-2-butenoic acid (3 g , 14.1 mmol) in dry methanol (300 mL ), cooled at 0° C., under dry nitrogen atmosphere, sodium methoxide (1.9 g , 35.2 mmol) dissolved in dry methanol (50 mL), was slowly added, on vigorous stirring and maintaining the temperature below 5° C. The resulting solution was stirred at 0° C. for one hour, then quenched with glacial acetic acid (1 mL) and evaporated in vacuo. The residue was taken up with ethyl acetate (100 mL), washed with 1N HCl (3×10 mL), brine (10 mL), dried (Na$_2$SO$_4$) and evaporated in vacuo to provide 3.2 g of crude product as colorless oily material.

Column flash chromatography (SiO$_2$; CH$_2$Cl$_2$/MeOH 98:2) afforded the pure acid (2.1 g , 62%); colorless prisms melting at 65–66° C.

Calcd. for C$_{11}$H$_{10}$ F$_2$O$_4$: C, 54.15; H, 4.13 found: C, 53.19; H, 4.33

MS, EI (m/z): 226.1 (M)$^+$·; 141.1 (C$_6$H$_3$F$_2$CO)$^+$·.

$^1$H NMR (200 MHz; d$_6$-DMSO), ppm: 3.25 (s, 3H); 3.23–3.45 (m, 2H); 4.18 (t,1H); 7.45–7.60 (m,1H); 7.80–8.0 (m, 2H); 12.8 (broad s, 1H).

Analogously, using sodium hydroxide instead of sodium methoxyde, the following compound can be prepared:

(R,S)-2-hydroxy-4-oxo-4-(3',4'-difluorophenyl)butanoic acid (PNU 158783) m.p. 111–112° C.

Calcd. for C$_{10}$H$_8$ F$_2$O$_4$: C, 52.18; H, 3.50 found: C, 52.34; H, 3.58

MS, FAB$^+$ (m/z): 231.5 (M+H)$^+$; 214.6; 141.3.

MS, FAB$^-$ (m/z): 229.6 (M+H)$^-$; 211.3 (M—H$_2$O—H)$^+$.

$^1$H NMR (200 MHz; d$_6$-DMSO), ppm: 3.23 (d, 2H); 4.42 (t, 1H); 7.58 (m,1H); 7.82 (m, 1H); 7.98 (m, 1H); 12.8 (broad s 1H).

Analogously, using sodium sulfide or sodium methylthiolate, the following compound can be prepared:

(R,S )-2-thio-4-oxo-4-(3',4'-difluorophenyl)butanoic acid. (R,S)-2-thiomethyl-4-oxo-4-(3',4'-difluorophenyl)butanoic acid.

Analogously, using sodium methoxide, 2-methoxy-4-oxo-4-(3',4'-dichlorophenyl)butanoic acid (PNU 157960), colorless needles, m.p. 98°–99° C., Calcd. for C$_{11}$H$_{10}$ Cl$_2$O$_4$: C, 47.70; H, 3.64; Cl, 25.63

Found: 47.84; 3.68; 25.79

MS (EI) m/z: 276 (M)$^+$·; 258 (M—H$_2$O)$^+$·; 173 (C$_6$H$_3$Cl$_2$CO)$^+$·.

$^1$H NMR (200 MHz; d$_6$-DMSO), ppm: 3.27 (3H, s); 3.38 (2H,m); 4.18 (1H, m); 7.76 (1H,d); 7.91 (1H,dd); 8.13 (1H,d); 12.80 (1H, broad s) was prepared starting from 4-oxo-4-(3',4'-dichlorophenyl)-2-butenoic acid (RN: 22660-10-2), which was in turn prepared according to Scheme 3 in 87% yield; yellow needles melting at 146–147° C. (toluene).

Analogously, using sodium hydroxide instead of sodium methoxyde, the following compound can be prepared:

(R,S)-2-hydroxy-4-oxo-4-(3',4'-dichlorophenyl)butanoic acid: (PNU 157695), colorless prisms, mp.150–151° C.

Calcd. for C$_{10}$H$_8$Cl$_2$O$_4$: C, 45.67; H, 3.07; Cl, 26.99

Found: 45.41; 3.16; 27.14

MS (FAB) m/z: 263.3 (M+H)$^+$.

$^1$H NMR (200 MHz; d$_6$-DMSO), ppm: 3.32 (2H, d); 4.43 (1H, t); 7.78 (1H,d); 7.93 (1H,dd); 8.18 (1H,d); 12.80 (1H, broad s).

Analogously, using sodium sulfide or sodium methylthiolate, the following compounds can be prepared:

(R,S)-2-thio-4-oxo-4-(3',4'-dichlorophenyl)butanoic acid; and (R,S)-2-thiomethyl-4-oxo-4-(3',4'-dichlorophenyl) butanoic acid.

EXAMPLE 4

(R,S)-2-chloro-4-(3',4'-dichlorophenyl)-4-oxo-butanoic acid (PNU 158781)

A solution of 4-oxo-4-(3',4'-dichlorophenyl)-2-butenoic acid (RN: 22660-10-2) (3.2 g, 13.1 mmol) in glacial acetic acid (320 mL), was saturated with dry HCl at 0° C., on stirring. The resulting solution was heated at 70° C. over 6 hours, during this time anhydrous hydrochloric acid was slowly bubbled through the solution. The reaction mixture was then evaporated in vacuo and the residue coevaporated from toluene. The resulting oily material was dissolved in diethyl ether and extracted with saturated sodium bicarbonate solution. The aqueous phase was washed with ether and the pH adjusted to 2 by addition of 37% HCl, the precipitated crude product was filtered, whased with water and dried. Recrystallization from toluene provided the pure acid as colorless solid, mp. 146–147° C.

$^1$H NMR (d$_6$-DMSO) ppm: 3.80 (m, 2H); 4.78 (t, 1H); 7.83 (d, 1H); 7.94 (dd, 1H); 8.18 (d, 1H); 13.1 (broad s, 1H):

MS (FAB)$^-$ m/z: 281.1 (M—H)$^-$; 243.1 (M—HCl—H)$^-$.

Calcd. for C$_{10}$H$_7$Cl$_3$O$_3$: C, 42.66; H, 2.51; Cl, 37.78 found: C, 43.04; H, 2.60; Cl, 37.26

Analogously, starting from 4-oxo-4-(3',4'-difluorophenyl)-2-butenoic acid, the following compound can be obtained:

(R,S)-2-chloro-4-(3',4'-difluorophenyl)-4-oxo-butanoic acid.

Analogously, using hydrofluoric acid instead of hydrochloric acid the following compounds can be obtained:

(R,S)-2-fluoro-4-(3',4'-dichlorophenyl)-4-oxo-butanoic acid; and (R,S)-2-fluoro-4-(3',4'-difluorophenyl)-4-oxo-butanoic acid.

EXAMPLE 5

(R,S)-Methyl-4-oxo-4-(3',4'-dichlorophenyl) butanoate (PNU 158381)

To a solution of 4-oxo-4-(3',4'-dichlorophenyl)butanoic acid (6 g, 27 mmol) in methanol (250 mL), 6N HCl methanolic solution (25 mL) was added at room temperature. The resulting solution was refluxed for 3 hours, then evaporated in vacuo. The obtained oily residue was dissolved in hexane/diisopropyl ether (80:20) on heating at reflux, the resulting solution was filtered, and cooled at room temperature. On standing at +5° C. the pure ester precipitated as colorless prisms (6.2 g, 88%), mp. 74–75° C.

Calcd. for C$_{11}$H$_{10}$ Cl$_2$O$_3$: C, 50.62; H, 3.86; Cl, 27.20 found: 51.57; 3.87; 26.97

MS, EI (m/z): 260.0 (M)$^+$·; 173.0 (C$_6$H$_3$Cl$_2$CO)$^+$.

$^1$H NMR (200 MHz; d$_6$-DMSO), ppm: 2.63 (2H, t ); 3.32 (2H, t); 3.60 (3H ,s); 7.80 (2H, d ); 7.94 (1H, dd ); 8.18 (1H, d).

EXAMPLE 6

(R,S)-Methyl-2-hydroxy-4-oxo-(3',4'-dichlorophenyl)butanoate (PNU 161211)

To a solution of (R,S)-Methyl-2-hydroxy-4-oxo-(3',4'-dichlorophenyl)butanoate (2.63 g, 10 mmol) in dry DMF (50 mL), under dry nitrogen atmosphere, DBU (2.7 mL, 18 mmol) was added on stirring at 0° C., followed by dropwise addition of iodomethane (6.2 mL, 0.1 mol). The resulting deep red solution was stirred at 0° C. over 2 hours, further stirring at room temperature an additional hour completed the reaction. The resulting mixture was poured into 0.5 N aqueous HCl/ice (1:1, w/w) and extracted with diethyl ether, the combined organic layers were whased with water, saturated bicarbonate solution, brine and dried ($Na_2SO_4$). Concentration of the solvent in vacuo, afforded an oily residue which crystallized on treatment with hexane/diisopropyl ether, to provide the pure ester (2.54 g, 91%), mp. 71–72° C.

Calcd. for $C_{11}H_{10}Cl_2O_4$: C, 47.69; H, 3.64; Cl, 25.60 found: 47.76; H, 3.76; 25.37

MS, $FAB^+$ (m/z): 277.1 $(M)^+$.

$^1$H NMR (200 MHz; $d_6$-DMSO), ppm: 3.38 (2H, d); 3.61 (3H, s); 4.53 (1H, q); 5.72 (1H,d); 7.78 (1H, d); 7.84 (1H, dd); 8.18 (1H, d).

EXAMPLE 7

(R,S)-2-hydroxy-4-oxo-4-(3'-chlorophenyl)butanoic acid (PNU 158789)

A well stirred mixture of 3-chloroacetophenone (18.9 g, 0.1 mol) and glyoxylic acid monohydrate (9.2 g, 0.1 mol) was heated at 60° C. under vacuum (25 mmHg), over 16 hours. The residue was taken up with diethyl ether and the organic phase was extracted with saturated $NaHCO_3$ solution, the combined aqueous layers were whased with ether, cooled at 0° C. and the pH of the solution was adjusted to 2 by addition of 37% HCl. The resulting suspension was extracted with ethyl acetate, and the combined organic extracts washed with water, drided ($Na_2SO_4$) and concentrated in vacuo to provide the crude product. Column chromatography ($SiO_2$; $CH_2Cl_2$/MeOH 95:5) afforded the pure titled compound as colorless needles, mp.98–100° C. (Diisopropyl ether/pentane).

Calcd. for $C_{10}H_9ClO_4$: C, 52.56; H, 3.97; Cl, 15.56; found: 52.35; H, 3.88; Cl, 15.16.

MS, $FAB^+$(m/z): 229.3 $(M)^+$.

MS, $FAB^-$(m/z): 227.1 $(M-H)^-$; 209.1 $(M-H_2O-H)^-$.

$^1$H NMR (200 MHz; $d_6$-DMSO), ppm: 3.32 (2H, d); 4.42 (1H, t); 7.53(1H, t); 7.72 (1H, dd); 7.91 (m, 2H); 12.80 (broad s, 1H).

Analogously, starting from the appropriate acetophenones, the following compounds can be obtained:

(R,S)-2-hydroxy-4-oxo-4-(3'-fluorophenyl)butanoic acid (PNU 158790): colorless prisms, mp.96–98° C. (diethyl ether/hexane).

Calcd. for $C_{10}H_9FO_4$: C, 56.65; H, 4.28; found: 56.51; H, 4.34.

MS, $FAB^+$(m/z): 213.4 $(M)^+$.

MS, $FAB^-$(m/z): 211.2 $(M)^-$; 193.1 $(M-H_2O-H)^-$.

$^1$H NMR (200 MHz; $d_6$-DMDO), ppm: 3.35 (2H, d); 4.43 (1H, t); 7.40–7.82(4H ,m ); 12.60 (broad s, 1H); and (R,S)-2-hydroxy-4-oxo-4-(3'-nitrophenyl)butanoic acid (PNU 158791): colorless solid, mp.139 –140° C.

Calcd. for $C_{10}H_9NO_6$: C, 50.26; H, 3.80; N, 5.86; found: 50.26; 3.93; 5.77.

MS ($FAB^-$) m/z: 238.2 $(M-H)^-$; 220.2 $(M-H_2O-H)^-$.

$^1$H, NMR (200 MHz; $d_6$-DMSO), ppm: 3.40 (2H, d); 4.53 (1H, t); 7.80(1H, t); 8.34–8.46 (2H, m); 8.61 (1H, d); 12.30–12.60 (broad s, 1H).

EXAMPLE 8

2-hydroxy-3-methyl-4-oxo-4-(3',4'-dichlorophenyl) butanoic acid (PNU 161244)

To a solution of 1-(3,4-dichlorophenyl)propanone (5.8 g, 28.5 mmol)in 95% ethanol (100 mL) a solution of glyoxylic acid monohydrate (2.63 g, 28.5 mmol) in water (20 mL) was added at 0° C., followed by dropwise addition of a solution of sodium hydroxide (4.6 g, 0.114 mol). The temperature during the addition was maintained below +5° C. on cooling. The resulting reaction mixture was stirred at 0° C. over 3 hours, then allowed to warm to room temperature and stirred further 12 hours. The most of ethanol was then removed under reduced pressure (15° C.), the residue was diluted with water and the pH of the obtained suspension adjusted to 2 by addition of 37% HCl, on stirring and cooling at 0° C. The aqueous phase was extracted with ethyl acetate, and the collected organic extracts were washed with brine, dried and evaporated to provide the crude reaction product as a light yellow oil (4.4 g). Column chromatography ($SiO_2$; $CH_2Cl_2$/MeOH 95:5) provided the pure titled compound (2.1 g, 27%), colorless solid (Ethyl ether/hexane) mp. 103–104° C.;

Calcd. for $C_{11}H_{10}Cl_2O_4$: C, 47.40; H, 3.64; Cl, 25.60; found: 47.86; H, 3.73; Cl, 25.64.

MS, EI (m/z): 280.0 $(M)^+$; 257.9 $(M-H_2O)^{+\cdot}$; 231.0 $(M-COOH)^+$; 172.9 $(C_6H_3Cl_2CO)^+$.

$^1$H NMR (200 MHz; $d_6$-DMSO), ppm: 1.08 (3H, d); 3.81 (1H, q); 4.18 (1H, d); 7.80–7.91(2H ,m); 8.09 (1H, d).

Analogously, starting from the appropriate ketones, the following compound can be obtained:

2-hydroxy-3-benzyl-4-oxo-4-(3',4'-dichlorophenyl) butanoic acid (PNU 167536): obtained from 1-(3',4'-dichlorophenyl)-3-phenyl propanone, colorless prisms, mp. 131–133° C.

Calcd. for $C_{17}H_{14}Cl_2O_4$: C, 57.83; H, 4.00; Cl, 20.08; found: 58.17; H, 3.87; Cl, 19.38.

$^1$H NMR (200 MHz; $d_6$-DMSO), ppm: 3.22 (2H, m); 4.11 (1H, m); 4.29 (1H, d); 7.18–7.30(5H ,m); 7.48 (1H,d); 7.62 (1H, dd). 7.89 (1H, d).

2-hydroxy-3-phenyl-4-oxo-4-(3',4'-dichlorophenyl) butanoic acid can be analogously prepared starting from from 1-(3',4'-dichlorophenyl)-2-phenyl ethanone.

EXAMPLE 9

4-(3'-nitrophenyl)-4-oxo-butanoic acid (PNU 157957)

To a suspension of triacetoxyborohydride (Aldrich) (21 g, 10 mmol) in dry THF (220 mL), a solution in dry THF (40 mL) of 4-(3'-nitrophenyl)-4-oxo-2-butenoic acid (2.2 g, 10 mmol)(prepared as described in example 7,(mp. 178–179° C.)), was added on stirring at room temperature, under dry nitrogen atmosphere. The resulting light yellow solution was stirred at room temperature overnight under nitrogen atmosphere. To the colorless reaction mixture, aqueos 1N HCl (50 mL), was slowly added dropwise, on cooling at 0° C. The most of the solvent was evaporated under reduced pressure and the residue taken up with 2N HCl and extracted with the ethyl acetate. The combined organic extracts were washed with brine, dried and concentrated in vacuo, to led to a solid. Recrystallization from diethyl ether/hexane afforded a cream solid (1.7 g ,77%), mp. 162–164° C.

Calcd. for $C_{10}H_9NO_6$: C, 53.81; H, 4.06; N, 6.27; found: 54.26; 4.18; 5.97.

MS ($FAB^-$) m/z: 222 $(M-H)^-$.

$^1$H NMR (200 MHz; $d_6$-DMSO), ppm: 2.63 (2H, t); 3.32 (2H, t); 7.80(1H ,t); 8.34–8.46 (2H, m); 8.61 (1H, d); 12.30–12.60 (broad s, 1H).

Analogously, the following compounds may be obtained starting from the appropriate compounds of formula (IV):

4-oxo-4-(3',4'-dichlorophenyl)butanoic acid (PNU 156588), m.p. 165–166° C.

Calcd. for $C_{10}H_8Cl_2O_3$: C, 48.63; H, 3.26; Cl, 28.74. Found: 48.71; 3.38; 27.98.

MS (FAB⁻) m/z: 245 (M−H)⁻.

$^1$H NMR (200 MHz; $d_6$-DMSO), ppm: 2.57 (2H, t); 3.23 (2H, t); 7.79 (1H, d); 7.92 (1H, dd); 8.18 (1H, s); 12.10 (1H, broad s);

4-oxo-4-(3'-chlorophenyl)butanoic acid; and
4-oxo-4-(3'-fluorophenyl)butanoic acid.

EXAMPLE 10

(R,S)-3-Methyl-4-oxo-4-(3',4'-dichlorophenyl) butanoic acid (PNU 161243)

3-Methyl-4-oxo-4-(3',4'-dichlorophenyl)-2-butenoic acid was prepared as below described. A well stirred mixture of 3'-chlorophenyl-1-propanone (12.9 g, 0.05 mol) and glyoxylic acid monohydrate (4.6 g, 0.05 mol) was heated for 22 hours at 120° C. under vacuum (0.1 mmHg), in order to remove the water formed during the reaction. The resulting dark red residue was dissolved in diethyl ether and the organic phase extracted with saturated $NaHCO_3$ solution, the combined alkaline extracts were whased with diethyl ether, to the stirred and cooled aqueous solution, 37% HCl was addeded dropwise until the pH of the solution was 1. The resulting suspension was extracted with ethyl acetate, and the combined organic extracts were washed with water, drided ($Na_2SO_4$) and concentrated in vacuo to provide the crude product. Column chromatography ($SiO_2$; $CH_2Cl_2$/MeOH 98:2) afforded the pure 3-Methyl-4-oxo-4-(3',4'-dichlorophenyl)-2-butenoic acid, (8.4 g, 65%), colorless plates, mp.143–144° C. (Toluene).

MS, EI (m/z): 258.0 (M)⁺˙; 223.0 (M−Cl⁻)⁺; 205.0 (M−Cl⁻—$H_2O$)⁺; 172.9 ($C_6H_3Cl_2CO$)⁺.

$^1$H NMR (200 MHz; $d_6$-DMSO), ppm: 2.20 (3H, s); 6.08 (1H, s); 7.63(1H, dd); 7.75 (1H, d); 7.90 (1H, d).

To a solution of 3-Methyl-4-oxo-4-(3',4'-dichlorophenyl)-2-butenoic acid (0.850 g, 3.3 mmol) in ethyl acetate (80 mL), Pd/C 5% (200 mg) is added, and the resulting suspension was hydrogenated at 30 p.s.i for 30 min. at room temperature. The catalyst was filtered and the filtrate concentrated in vacuo to an oily residue. Column chromatography ($SiO_2$; $CH_2Cl_2$/MeOH 96:4) afforded the pure 3-Methyl-4-oxo-4-(3',4'-dichlorophenyl)butanoic acid (0.625 g, 73%), colorless needles, mp.124–126° C.

Calcd. for $C_{11}H_{10}Cl_2O_3$: C, 50.60; H, 3.86; Cl, 27.16; found: 51.19; 3.98; 26.97.

MS, EI (m/z): 260.0 (M)⁺˙; 172.9 ($C_6H_3Cl_2CO$)⁺.

$^1$H NMR (200 MHz; $d_6$-DMSO), ppm: 1.08 (3H, d); 2.38–2.79 (2H, m); 3.80 (1H, m); 7.78(1H, d); 7.89 (1H, dd); 8.12 (1H, d); 12.30 (1H, broad s).

Analogously, starting from the appropriate compound of formula (IV), the following compound can be obtained:

(R,S)-3-Phenyl-4-oxo-4-(3',4'-dichlorophenyl)butanoic acid (PNU 167541).

The corresponding 3-Phenyl-4-oxo-4-(3',4'-dichlorophenyl)-2-butenoic acid was obtained as above described, m.p. 101–103° C., starting from 1-(3',4'-dichlorophenyl)-2-phenyl ethanone. Reduction of the unsaturated acid afforded the corresponding butanoic acid (PNU 167541): colorless prisms, mp. 147–148° C.

Calcd. for $C_{16}H_{12}Cl_2O_3$: C, 59.49; H, 3.74; Cl, 22.95; found: 59.46; 3.79; 22.96.

$^1$H NMR (200 MHz; $d_6$-DMSO), ppm: 2.74 (1H, dd); 3.42 (1H, dd); 4.93 (1H, m); 7.21(5H, m); 7.43 (1H, d); 7.88 (1H, dd); 8.12 (1H, d).

(R,S)-3-Benzyl-4-oxo-4-(3',4'-dichlorophenyl)butanoic acid can be analogously obtained starting from 1-(3',4,'-dichlorophenyl)-3-phenyl propanone.

EXAMPLE 11

Methyl (R,S)-2-Phenyl-4-oxo-4-(3',4'-dichlorophenyl)butanoate (PNU 166928)

To a stirred suspension of cuprous bromide dimethylsulfide complex (Fluka)(0.870 g, 4.2 mmol)in dry THF (50 mL), 1.8 M, phenylmagnesium bromide solution in THF (mL 7.0, 12.6 mmol) was added dropwise over 10 min., under dry nitrogen atmosphere, at 0° C. The resulting solution was cooled at −30° C. and Methyl (E)-4-oxo-4-(3', 4'-dichlorophenyl)butanoate (2.2 g, 8.5 mmol) dissolved in dry THF (120 mL), was slowly added dropwise, maintaining the reaction temperature below −25° C. During the addition the color of the reaction mixture turned from deep green to cream. Completed the addition the resulting solution was allowed to warm to room temperature and the reaction was quenched in 20% $NH_4Cl$/ice. The resulting slurry was extracted with diethyl ether and the combined organic extracts were washed with brine dried and concentrated under reduced pressure to a pale yellow oil. Column chromatography ($SiO_2$; hexane/diethyl ether,90:10) led to the pure methylester (2.2 g; 78%) as a colorless oil, which crystallized on treatment with diisopropyl ether/hexane, colorless plates, mp. 81–82° C.

Calcd. for $C_{17}H_{14}Cl_2O_3$: C, 60.53; H, 4.15; Cl, 21.07; found: 60.92; 4.33; 21.08.

MS, EI (m/z): 336.0 (M)⁺˙; 304 (M−$CH_3OH$)⁺˙; 173.0 ($C_6H_3Cl_2CO$)⁺.

$^1$H NMR (200 MHz; $d_6$-DMSO), ppm: 3.40 (1H, dd); 3.58 (3H, s); 3.96 (1H, dd); 4.18 (1H, dd); 7.23–7.40 (5H, m); 7.78(1H, d); 7.89 (1H, dd); 8.12 (1H, d).

Analogously, Methyl (R,S)-2-Benzyl-4-oxo-4-(3',4'-dichlorophenyl)butanoate (PNU 167531) was prepared using benzyl magnesium bromide instead of pheny magnesium bromide. Colorless prisms, mp.72–73° C.

Calcd. for $C_{18}H_{16}Cl_2O_3$: C, 61.55; H, 4.59; Cl, 20.19; found: 61.92; 4.73; 20.02.

MS, EI (m/z): 350.0 (M)⁺˙; 318.0 (M−$CH_3OH$)⁺˙; 173.0 ($C_6H_3Cl_2CO$)⁺.

$^1$H NMR (200 MHz; $d_6$-DMSO), ppm: 2.80–2.93(1H, m); 2.91 (1H, d); 3.13 (1H, dd); 3.37 (1H, m); 3.39 (1H, d); 3.65 (3H, s); 7.09–7.24 (5H, m); 7.72(1H, d); 7.78 (1H, dd); 7.97 (1H, d).

EXAMPLE 12

(R,S)-2-Phenyl-4-oxo-4-(3',4'-dichlorophenyl) butanoic acid (PNU 167533)

To a solution of Methyl (R,S)-2-Phenyl-4-oxo-4-(3',4'-dichlorophenyl)butanoate (1.8 g, 5.3 mmol) in methanol (80 mL) cooled at 0° C., aqueous 1N, sodium hydroxide (10.6 mL, 10.6 mmol) was added dropwise on stirring. The resulting reaction mixture was stirred at 0° C. 1 hour, then allowed to warm to room temperature and stirred further 3 hours. The most of the solvent was evaporated under reduced pressure and the residue diluted with water. The resulting solution was acidified with 37% HCl to pH 2 and extracted with diethyl ether, the combined organic extracts were washed with brine dried and concentrated to a colorless solid (1.8 g). Recrystallization from diethyl ether afforded the pure acid (1.4 g, 83%), colorless needles, mp.166–167° C.

Calcd. for $C_{16}H_{12}Cl_2O_3$: C, 59.47; H, 3.74; Cl, 21.94; found: 59.47; 3.82; 21.64.

MS, EI (m/z): 322.0 $(M)^{+\cdot}$; 304.0 $(M-H_2O)$; 275.0 $(M-COOH)^+$; 173.0 $(C_6H_3Cl_2CO)^+$.

$^1$H NMR (200 MHz; $d_6$-DMSO), ppm: 3.23 (1H, dd); 3.80–4.09 (2H, m); 7.10–7.2 (5H, m); 7.78 (1H, d); 7.94 (1H, dd); 8.22 (1H, d).

Analogously, (R,S) 2-Benzyl-4-oxo-4-(3',4'-dichlorophenyl) butanoic acid (PNU 167531) was prepared starting from Methyl (R,S)-2-Benzyl-4-oxo-4-(3',4'-dichlorophenyl)butanoate Colorless prisms, mp.147–148° C.

Calcd. for $C_{17}H_{14}Cl_2O_3$: C, 60.55; H, 4.18; Cl, 21.03; found: 60.92; 4.32; 20.74.

MS, EI (m/z): 336.0 $(M)^{+\cdot}$; 289.0 $(M-COOH)^+$; 173.0 $(C_6H_3Cl_2CO)_+$.

$^1$H NMR (200 MHz; $d_6$-DMSO), ppm: 2.80–3.94 (2H, m); 3.20–3.40 (3H, m); 7.10–7.15 (5H, m); 7.50 (1H, d); 7.67 (1H, dd); 7.97 (1H, d).

EXAMPLE 13

Capsule, each weighing 0.23 g and containing 50 mg of the active substance can be prepared as follows:

Composition for 500 capsules:

| | |
|---|---|
| 4-(3',4'-dichlorophenyl)-4-oxo-butanoic acid | 25 g |
| Lactose | 80 g |
| Corn starch | 5 g |
| Magnesium stearate | 5 g |

This formulation can be incapsulated in two hard gelatin capsules of two pieces, each with each capsule weighing 0.23 g.

EXAMPLE 14

Intramuscular Injection of 50 mg/ml

A pharmaceutical injectable composition can be manifactured dissolving 50 g of 4-(3',4'-dichlorophenyl)-4-oxo-butanoic acid in sterile propyleneglycol (1000 ml) and sealed in 1–5 ml ampoules.

Legend to FIG. 1, which shows Kynurenine pathway
IDO: Indolamineoxygenase,
KYN: kynurenine
KYN-3-OHase: Kynurenine-3-hydroxylase
KYN-3-OH: 3-hydroxy kynurenine
KAT: Kynurenine amino transferase
3-OHAA: 3-hydroxy anthranilic acid
KYNase: Kynureninase
3-HAO: 3-hydroxy anthranilic acid dioxygenase
KYNA: Kynurenic acid
QUIN: quinolinic acid
TDO: tryptophanedioxygenase

What is claimed is:
1. A 4-phenyl-4-oxo-butanoic acid compound of formula (IA):

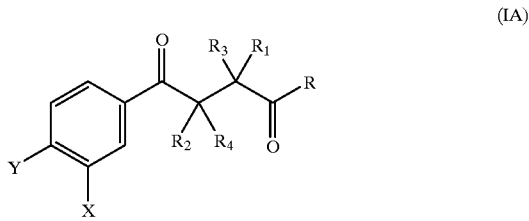

either as single isomer, as a mixture of isomers thereof, or as a pharmaceutically acceptable salt thereof wherein:
X and Y are, each independently, fluorine or chlorine;
R is hydroxy; $-OR_5$ in which $R_5$ is $C_1-C_6$ alkyl, phenyl benzyl, $C_2-C_4$ alkenyl or $C_2-C_4$ alkynyl; $-N(R_6)_2$ or $-N(R_6)OR_6$ in which each of $R_6$ is hydrogen, $C_1-C_6$ alkyl, $C_2-C_4$ alkenyl, $C_2-C_4$ alkynyl, phenyl or benzyl;
$R_1$, $R_2$, $R_3$ and $R_4$ are, each independently, hydrogen, halogen hydroxy, cyano, thiol, $C_1-C_6$alkoxy, $C_1-C_6$ alkylthio, $C_1-C_6$ alkyl $C_2-C_4$ alkenyl, phenyl or benzyl, or
$R_1$ and $R_3$ or $R_2$ and $R_4$ together form a group $=CHR_8$ in which $R^8$ is hydrogen, a straight $C_1-C_5$ alkyl chain or phenyl;
provided that:
(i) when X and Y are both chlorine and $R_1$, $R_2$ and $R_4$ are simultaneously hydrogen, $R_3$ is different from hydrogen, hydroxy, methoxy, ethylthio or isopropy-lthio; and
(ii) when X and Y are both fluorine, $R_1$, $R_2$, $R_3$ and $R_4$ are not simultaneously hydrogen.
2. A compound as claimed in claim 1, wherein
X and Y are, each independently, fluorine or chlorine;
R is hydroxy or $-OR_5$ in which $R_5$ is $C_1-C_6$ alkyl;
$R_1$, $R_2$, $R_3$ and $R_4$ are, each independently, hydrogen, halogen, cyano, hydroxy, thiol, $C_1-C_6$ alkoxy, $C_1-C_6$ alkylthio, $C_1-C_6$ alkyl, phenyl, benzyl or $C_2-C_4$ alkenyl, or
$R_1$ and $R_3$ or $R_2$ and $R_4$ together form a group $=CHR_8$ in which $R_8$ is hydrogen, a straight $C_1-C_5$ alkyl or phenyl; or a pharmaceutically acceptable salt thereof.
3. A pharmaceutical composition comprising the compound of claim 1 or a pharmaceutically acceptable salt thereof, and a pharmaceutically acceptable carrier or diluent.
4. A compound selected from the group consisting of:

2-hydroxy-4-(3',4'-difluorophenyl)-4-oxo-butanoic acid;
2-methoxy-4-(3',4'-difluorophenyl)-4-oxo-butanoic acid;
2-hydroxy-3-methyl-4-(3',4'-dichlorophenyl)-4-oxo-butanoic acid;
2-hydroxy-3-phenyl-4-(3',4'-dichlorophenyl)-4-oxo-butanoic acid;
2-hydroxy-3-benzyl-4-(3',4'-dichlorophenyl)-4-oxo-butanoic acid;
2-methyl-4-(3',4'-dichlorophenyl)-4-oxo-butanoic acid;
2-methyl-4-(3',4'-difluororophenyl)-4-oxo-butanoic acid;
2-chloro-4-(3',4'-dichlorophenyl)-4-oxo-butanoic acid;
2-chloro-4-(3',4'-difluorophenyl)-4-oxo-butanoic acid;
2-fluoro-4-(3',4'-dichlorophenyl)-4-oxo-butanoic acid;
2-fluoro-4-(3',4'-difluorophenyl)-4-oxo-butanoic acid;
2-thiomethyl-4-(3',4'-dichlorophenyl)-4-oxo-butanoic acid;
2-methyliden-4-(3',4'-dichlorophenyl)-4-oxo-butanoic acid;

2-phenyl-4-(3',4'-dichlorophenyl)-4-oxo-butanoic acid;
2-benzyl-4-(3',4'-dichlorophenyl)-4-oxo-butanoic acid;
3-methyl-4-(3',4'-dichlorophenyl)-4-oxo-butanoic acid;
3-methyl-4-(3',4'-dichlorophenyl)-4-oxo-butanoic acid;
3-phenyl-4-(3',4'-dichlorophenyl)-4-oxo-butanoic acid;
3-benzyl-4-(3',4'-dichloropheny )-4-oxo-butanoic acid;
(R,S)-methyl-2-hydroxy-4-(3',4'-dichlorophenyl)-4-oxo-butanoate; and
(R,S)-methyl-2-benzyl-4-(3',4'-dichlorophenyl)-4-oxo-butanoate;

wherein said compounds may be single isomers, isomer mixtures, or pharmaceutically acceptable salts thereof.

5. A method of inhibiting kynurenine-3-hydroxylase comprising providing or administering, to a patient in need thereof, an effective amount of a 4-phenyl-oxo-butanoic acid compound of formula (I):

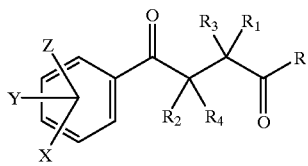
(I)

either as a single isomer, as a mixture of isomers thereof, or as pharmaceutically acceptable salt wherein:

X, Y and Z are, each independently, hydrogen, halogen, cyano, nitro, $C_1$–$C_6$ alkyl, phenyl, benzyl, $C_2$–$C_4$ alkenyl, $C_2$–$C_4$ alkynyl, $C_1$–$C_6$ alkoxy or $C_1$–$C_6$ alkylthio;

R is hydroxy; —$OR_5$ in which $R_5$ is $C_1$–$C_6$ alkyl, phenyl, benzyl, $C_2$–$C_4$ alkenyl or $C_2$–$C_4$ alkynyl; —$N(R_6)_2$ or —$N(R_6)OR_6$ in which each $R_6$ is, independently, hydrogen, $C_1$–$C_6$ alkyl, $C_2$–$C_4$ alkenyl, $C_2$—$C_4$ alkynyl, phenyl or benzyl;

$R_1$, $R_2$, $R_3$ and $R_4$ are, each independently, hydrogen, halogen, hydroxy, thiol, $C_1$–$C_6$ alkoxy, $C_1$–$C_6$ alkylthio, $C_1$–$C_6$ alkyl, $C_2$–$C_4$ alkenyl, phenyl or benzyl, or $R_1$ and $R_3$ or $R_2$ and $R_4$ together form a group =$CHR_8$ in which $R_8$ is hydrogen, a straight $C_1$–$C_5$ alkyl chain or phenyl; and wherein when, at the same time, X is hydrogen, halogen or phenyl; Y is hydrogen or $C_1$–$C_6$ alkoxy; $R_1$ and $R_3$ together form a =$CH_2$ group and R is hydroxy or $C_1$–$C_6$ alkoxy, then at least one of Z, $R_2$ and $R_4$ is other than hydrogen;

wherein when, at the same time, X is hydrogen, halogen, $C_1$–$C_6$ alkyl or $C_1$–$C_6$ alkoxy; Y is phenyl; $R_3$ is methyl and Z, $R_1$, $R_2$ and $R_4$ are hydrogen, then R is other than hydroxy; and wherein when, at the same time, Y is isopropyl or tertiary-butyl; X is chlorine or nitro; R is hydroxy, $C_1$–$C_6$ alkoxy or alkoxy or —$N(R_6)_2$ in which each $R_6$ is hydrogen or $C_1$–$C_6$ alky then at least one of $R_1$, $R_2$ $R_3$, $R_4$ and Z is other than hydrogen.

6. A method of preventing and/or treating a neurodegenerative disease comprising providing or administering, to a patient in need thereof, an effective amount of a 4-phenyl-oxo-butanoic acid compound

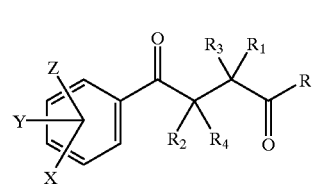
(I)

of formula (I): either as a single isomer, as a mixture of isomers, or as pharmaceutically acceptable salt thereof wherein:

X, Y and Z are, each independently, hydrogen, halogen, cyano, nitro, $C_1$–$C_6$ alkyl, phenyl, benzyl, $C_2$–$C_4$ alkenyl, $C_2$–$C_4$ alkynyl, $C_1C_6$ alkoxy or $C_1$–$C_6$ alkylthio;

R is hydroxy; —$OR_5$ in which $R_5$ is $C_1$–$C_6$ alkyl, phenyl, benzyl, $C_2$–$C_4$ alkenyl or $C_2C_4$ alkynyl; —$NR_6)_2$ or —$NR_6)OR_6$ in which each $R_6$ is, independently, hydrogen, $C_1$–$C_6$ alkyl, $C_2$–$C_4$ alkenyl, $C_2$–$C_4$ alkynyl, phenyl or benzyl;

$R_1$, $R_2$, $R_3$ and $R_4$ are, each independently, hydrogen, halogen, hydroxy, thiol, $C_1$–$C_6$ alkoxy, $C_1$–$C_6$ alkylthio, $C_1$–$C_6$ alkyl, $C_2$–$C_4$ alkenyl, phenyl or benzyl, or $R_1$ and $R_3$ or $R_2$ and $R_4$ together form a group =$CHR_8$ in which $R_8$ is hydrogen, a straight $C_1$–$C_5$ alkyl chain or phenyl; and wherein when, at the same time, X is hydrogen, halogen or phenyl; Y is hydrogen or $C_1$–$C_6$ alkoxy; $R_1$ and $R_3$ together form a =$CH_2$ group and R is hydroxy or $C_1$–$C_6$ alkoxy, then at least one of Z, $R_2$ and $R_4$ is other than hydrogen;

wherein when, at the same time, X is hydrogen, halogen, $C_1$–$C_6$ alkyl or $C_1$–$C_6$ alkoxy; Y is phenyl; $R_3$ is methyl and Z, $R_1$, $R_2$ and $R_4$ are hydrogen, then R is other than hydroxy; and wherein when, at the same time, Y is isopropyl or tertiary-butyl; X is chlorine or nitro; R is hydroxy, $C_1$–$C_6$ alkoxy or alkoxy or —$N(R_6)_2$ in which each $R_6$ is hydrogen or $C_1$–$C_6$ alky then at least one of $R_1$, $R_2$, $R_3$, $R_4$ and Z is other than hydrogen.

7. The method according to claim 6, wherein the neurodegenerative disease is:

Huntington's chorea, Alzheimer's disease, dementia caused by Acquired Immunodeficiency Syndrome (AIDS), infarctual dementia, cerebral ischemia, cerebral hypoxia, Parkinson's disease epilepsy, head and spinal cord injury, amyotrophic lateral sclerosis, glaucoma retinopathy, infections of the brain or inflammations of the brain.

8. A method of inhibiting kynurenine-3-hydroxylase comprising providing or administering, to a patient in need thereof, an effective amount of the compound as claimed in claim 1, or a pharmaceutically acceptable salt thereof.

9. A method of treating a patient in need of a kynurenine-3-hydroxylase inhibitor comprising providing or administering, to a patient in need thereof, to said patient an effective amount of the compound according to claim 1, or a pharmaceutically acceptable salt thereof.

10. A method of preventing and/or treating a neurodegenerative disease comprising providing or administering, to a patient in need thereof, an effective amount of the compound as claimed in claim 1 or a pharmaceutically acceptable salt thereof.

11. The method of claim 9 wherein the neurodegenerative disease is Huntington's chorea, Alzheimer's disease, dementia caused by Acquired Immunodeficiency Syndrome (AIDS), infarctual dementia, cerebral ischemia, cerebral hypoxia, Parkinson's disease, epilepsy, head and spinal cord injury, amyotrophic lateral sclerosis, glaucoma retinopathy, infections of the brain or inflammations of the brain.

12. A method of inhibiting kynurenine-3-hydroxylase comprising providing or administering, to a patient in need thereof, an effective amount of the compound of claim 4.

13. A method of preventing and/or treating a neurodegenerative disease comprising providing or administering, to patient in need thereof, an effective amount of the compound of claim 4.

14. The method of claim 13 wherein the neurodegenerative disease is Huntington's chorea, Alzheimer's disease, dementia caused by Acquired Immunodeficiency Syndrome (AIDS), infarctual dementia, cerebral ischemia, cerebral hypoxia, Parkinson's disease, epilepsy, head and spinal cord injury, amyotrophic lateral sclerosis, glaucoma retinopathy, infections of the brain or inflammations of the brain.

* * * * *